(12) United States Patent
Bapna et al.

(10) Patent No.: US 12,349,966 B2
(45) Date of Patent: **\*Jul. 8, 2025**

(54) METHODS AND DEVICES FOR ENDOVASCULAR ABLATION OF A SPLANCHNIC NERVE

(71) Applicant: Axon Therapies, Inc., New York, NY (US)

(72) Inventors: Anisha Bapna, Edison, NJ (US); Zoar Jacob Engelman, New York, NY (US); Howard Levin, Teaneck, NJ (US); Pajhand Iranitalab, San Ramon, CA (US); Casey Andrew Miller, Campbell, CA (US); Thomas Ryan McGrath, Santa Clara, CA (US); Manuel Arzadon Javier, Jr., Santa Clara, CA (US)

(73) Assignee: AXON THERAPIES, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/476,028

(22) Filed: Sep. 27, 2023

(65) Prior Publication Data

US 2024/0206963 A1 Jun. 27, 2024

Related U.S. Application Data

(63) Continuation of application No. 17/451,991, filed on Oct. 22, 2021, now Pat. No. 11,806,073, which is a
(Continued)

(51) Int. Cl.
*A61B 18/14* (2006.01)
*A61B 6/00* (2024.01)
(Continued)

(52) U.S. Cl.
CPC ............ *A61B 18/1492* (2013.01); *A61B 6/12* (2013.01); *A61B 6/4441* (2013.01); *A61B 6/481* (2013.01);
(Continued)

(58) Field of Classification Search
CPC ...... A61B 18/1492; A61B 2018/00011; A61B 2018/0022; A61B 2018/00267;
(Continued)

(56) References Cited

U.S. PATENT DOCUMENTS

| 3,301,258 A | 1/1967 | Werner |
| 4,403,985 A | 9/1983 | Boretos |

(Continued)

FOREIGN PATENT DOCUMENTS

| CN | 1219855 A | 6/1999 |
| CN | 1269708 A | 10/2000 |

(Continued)

OTHER PUBLICATIONS

Piciucchi et al. ("the azygos vein pathway: an overview from anatomical variations of pathological changes"; Insights Imaging (2014) 5:619-628).*

(Continued)

*Primary Examiner* — Shahdeep Mohammed
(74) *Attorney, Agent, or Firm* — Nixon & Vanderhye P.C.

(57) ABSTRACT

Systems, devices, and methods for transvascular ablation of target tissue. The devices and methods may, in some examples, be used for splanchnic nerve ablation to increase splanchnic venous blood capacitance to treat at least one of heart failure and hypertension. For example, the devices disclosed herein may be advanced endovascularly to a target vessel in the region of a thoracic splanchnic nerve (TSN), such as a greater splanchnic nerve (GSN) or a TSN nerve root. Also disclosed are methods of treating heart failure,
(Continued)

such as HFpEF, by endovascularly ablating a thoracic splanchnic nerve to increase venous capacitance and reduce pulmonary blood pressure.

8 Claims, 14 Drawing Sheets

Related U.S. Application Data continuation of application No. PCT/US2020/038934, filed on Jun. 22, 2020.

(60) Provisional application No. 62/881,251, filed on Jul. 31, 2019, provisional application No. 62/864,093, filed on Jun. 20, 2019.

(51) Int. Cl.
*A61B 6/12* (2006.01)
*A61B 6/50* (2024.01)
*A61B 18/00* (2006.01)
*A61B 34/20* (2016.01)
*A61B 90/00* (2016.01)

(52) U.S. Cl.
CPC .............. *A61B 6/504* (2013.01); *A61B 34/20* (2016.02); *A61B 90/39* (2016.02); *A61B 2018/00404* (2013.01); *A61B 2018/00577* (2013.01); *A61B 2034/2065* (2016.02); *A61B 2090/3966* (2016.02)

(58) Field of Classification Search
CPC ........... A61B 2018/00404; A61B 2018/00434; A61B 2018/00577; A61B 2018/00791; A61B 2018/00994; A61B 2018/0212; A61B 2034/2065; A61B 2090/3966; A61B 2218/002; A61B 34/20; A61B 6/12; A61B 6/4441; A61B 6/481; A61B 6/504; A61B 90/39; A61N 7/022
See application file for complete search history.

(56) References Cited

U.S. PATENT DOCUMENTS

| | | |
|---|---|---|
| 4,862,891 A | 9/1989 | Smith |
| 5,447,529 A | 9/1995 | Marchlinski et al. |
| 5,454,840 A | 10/1995 | Krakovsky et al. |
| 5,458,626 A | 10/1995 | Krause |
| 5,462,545 A | 10/1995 | Wang et al. |
| 5,536,240 A | 7/1996 | Edwards et al. |
| 5,558,673 A | 9/1996 | Edwards et al. |
| 5,569,198 A | 10/1996 | Racchini |
| 5,649,974 A | 7/1997 | Nelson et al. |
| 5,658,282 A | 8/1997 | Daw et al. |
| 5,704,908 A | 1/1998 | Hofmann et al. |
| 5,722,403 A | 3/1998 | McGee et al. |
| 5,740,808 A | 4/1998 | Panescu et al. |
| 5,797,903 A | 8/1998 | Swanson et al. |
| 5,800,484 A | 9/1998 | Gough et al. |
| 5,830,213 A | 11/1998 | Panescu et al. |
| 5,836,874 A | 11/1998 | Swanson et al. |
| 5,840,076 A | 11/1998 | Swanson et al. |
| 5,846,239 A | 12/1998 | Swanson et al. |
| 5,860,974 A | 1/1999 | Abele |
| 5,868,736 A | 2/1999 | Swanson et al. |
| 5,871,483 A | 2/1999 | Jackson et al. |
| 5,891,136 A | 4/1999 | McGee et al. |
| 5,925,038 A | 7/1999 | Panescu et al. |
| 5,928,229 A | 7/1999 | Gough et al. |
| 5,961,513 A | 10/1999 | Swanson et al. |
| 6,044,846 A | 4/2000 | Edwards |
| 6,058,331 A | 5/2000 | King |
| 6,071,278 A | 6/2000 | Panescu et al. |
| 6,099,526 A | 8/2000 | Whayne et al. |
| 6,123,718 A | 9/2000 | Tu et al. |
| 6,165,172 A | 12/2000 | Farley et al. |
| 6,236,886 B1 | 5/2001 | Cherepenin et al. |
| 6,395,325 B1 | 5/2002 | Hedge et al. |
| 6,409,722 B1 | 6/2002 | Hoey et al. |
| 6,425,877 B1 | 7/2002 | Edwards |
| 6,454,766 B1 | 9/2002 | Swanson et al. |
| 6,475,213 B1 | 11/2002 | Whayne et al. |
| 6,569,160 B1 | 5/2003 | Goldin et al. |
| 6,638,275 B1 | 10/2003 | McGaffigan et al. |
| 6,656,174 B1 | 12/2003 | Hegde et al. |
| 6,658,279 B2 | 12/2003 | Swanson et al. |
| 6,658,929 B2 | 12/2003 | Atkinson |
| 6,668,198 B2 | 12/2003 | Swanson et al. |
| 6,743,197 B1 | 6/2004 | Edwards |
| 6,760,616 B2 | 7/2004 | Hoey et al. |
| 6,832,114 B1 | 12/2004 | Whitehurst et al. |
| 6,849,073 B2 | 2/2005 | Hoey et al. |
| 6,885,888 B2 | 4/2005 | Rezai |
| 6,890,315 B1 | 5/2005 | Levin et al. |
| 6,954,977 B2 | 10/2005 | Maguire et al. |
| 6,984,232 B2 | 1/2006 | Vanney et al. |
| 7,054,689 B1 | 5/2006 | Whitehurst et al. |
| 7,104,989 B2 | 9/2006 | Skarda |
| 7,149,574 B2 | 12/2006 | Yun et al. |
| 7,153,301 B2 | 12/2006 | Swartz et al. |
| 7,236,822 B2 | 6/2007 | Dobak, III |
| 7,239,912 B2 | 7/2007 | Dobak, III |
| 7,282,050 B2 | 10/2007 | Starkebaum et al. |
| 7,282,051 B2 | 10/2007 | Rioux et al. |
| 7,285,199 B2 | 10/2007 | Mitsuhashi et al. |
| 7,326,208 B2 | 2/2008 | Vanney et al. |
| 7,330,762 B2 | 2/2008 | Boveja et al. |
| 7,335,377 B2 | 2/2008 | Stern et al. |
| 7,367,972 B2 | 5/2008 | Francischelli et al. |
| 7,416,549 B2 | 8/2008 | Young et al. |
| 7,418,292 B2 | 8/2008 | Shafer |
| 7,427,280 B2 | 9/2008 | Gerber |
| 7,449,018 B2 | 11/2008 | Kramer |
| 7,529,582 B1 | 5/2009 | DiLorenzo |
| 7,532,938 B2 | 5/2009 | Machado et al. |
| 7,551,964 B2 | 6/2009 | Dobak, III |
| 7,599,736 B2 | 10/2009 | DiLorenzo |
| 7,623,924 B2 | 11/2009 | Narciso, Jr. |
| 7,689,276 B2 | 3/2010 | Dobak |
| 7,689,277 B2 | 3/2010 | Dobak, III |
| 7,702,386 B2 | 4/2010 | Dobak et al. |
| 7,736,362 B2 | 6/2010 | Ebert et al. |
| 7,769,442 B2 | 8/2010 | Shafer |
| 7,778,703 B2 | 8/2010 | Gross et al. |
| 7,860,570 B2 | 12/2010 | Whitehurst et al. |
| 7,865,237 B2 | 1/2011 | Machado et al. |
| 7,877,146 B2 | 1/2011 | Rezal et al. |
| 7,921,657 B2 | 4/2011 | Littrup et al. |
| 7,937,145 B2 | 5/2011 | Dobak |
| 8,007,496 B2 | 8/2011 | Rioux et al. |
| 8,155,744 B2 | 4/2012 | Rezai |
| 8,241,273 B2 | 8/2012 | Whayne et al. |
| 8,270,568 B2 | 9/2012 | Pitt |
| 8,295,926 B2 | 10/2012 | Dobak, III |
| 8,321,030 B2 | 11/2012 | Maniak et al. |
| 8,399,443 B2 | 3/2013 | Seward |
| 8,401,667 B2 | 3/2013 | Gustus et al. |
| 8,414,508 B2 | 4/2013 | Thapliyal et al. |
| 8,433,412 B1 | 4/2013 | Westlund et al. |
| 8,473,051 B1 | 6/2013 | Wessels et al. |
| 8,483,835 B2 | 7/2013 | Errico et al. |
| 8,611,496 B2 | 12/2013 | Terunuma et al. |
| 8,676,326 B1 | 3/2014 | Farazi |
| 8,676,362 B2 | 3/2014 | Gabel et al. |
| 8,798,738 B2 | 8/2014 | Machado et al. |
| 8,814,793 B2 | 8/2014 | Brabrand |
| 8,911,439 B2 | 12/2014 | Mayse et al. |
| 8,994,536 B2 | 3/2015 | Margon |
| 8,998,894 B2 | 4/2015 | Mauch et al. |
| 9,005,100 B2 | 4/2015 | Gnanashanmugam et al. |
| 9,022,948 B2 | 5/2015 | Wang |
| 9,028,472 B2 | 5/2015 | Mathur et al. |

(56) References Cited

U.S. PATENT DOCUMENTS

| | | |
|---|---|---|
| 9,033,969 B2 | 5/2015 | Azamian et al. |
| 9,037,259 B2 | 5/2015 | Mathur |
| 9,072,902 B2 | 7/2015 | Mathur et al. |
| 9,125,661 B2 | 9/2015 | Deem |
| 9,125,668 B2 | 9/2015 | Subramaniam et al. |
| 9,162,075 B2 | 10/2015 | Sluijter et al. |
| 9,174,050 B2 | 11/2015 | Mathur et al. |
| 9,199,091 B2 | 12/2015 | Danek et al. |
| 9,245,182 B2 | 1/2016 | Jania et al. |
| 9,278,196 B2 | 3/2016 | Fischell et al. |
| 9,345,530 B2 | 5/2016 | Ballakur et al. |
| 9,345,900 B2 | 5/2016 | Wu et al. |
| 9,370,657 B2 | 6/2016 | Tehrani et al. |
| 9,439,580 B2 | 9/2016 | Hatlestad et al. |
| 9,439,598 B2 | 9/2016 | Shimada et al. |
| 9,592,386 B2 | 3/2017 | Mathur et al. |
| 9,603,659 B2 | 3/2017 | Subramaniam et al. |
| 9,743,845 B2 | 8/2017 | Wang |
| 9,757,193 B2 | 9/2017 | Zarins et al. |
| 9,895,539 B1 | 2/2018 | Heit et al. |
| 10,207,110 B1 | 2/2019 | Gelfand et al. |
| 10,376,308 B2 | 8/2019 | Levin et al. |
| 10,561,461 B2 | 2/2020 | Panescu et al. |
| 10,912,610 B2 | 2/2021 | Levin et al. |
| 11,154,354 B2 | 10/2021 | Levin et al. |
| 11,376,066 B2 | 6/2022 | Levin et al. |
| 11,413,090 B2 | 8/2022 | Iranitalab et al. |
| 11,504,185 B2 | 11/2022 | Iranitalab et al. |
| 11,712,296 B2 | 8/2023 | Panescu et al. |
| 11,751,939 B2 | 9/2023 | Panescu et al. |
| 11,801,092 B2 | 10/2023 | Levin et al. |
| 11,806,073 B2 | 11/2023 | Bapna et al. |
| 11,844,569 B1 | 12/2023 | Panescu et al. |
| 2001/0056274 A1* | 12/2001 | Perkins ............... A61B 50/30 604/118 |
| 2002/0087152 A1 | 7/2002 | Mikus et al. |
| 2002/0165532 A1 | 11/2002 | Hill et al. |
| 2002/0198520 A1 | 12/2002 | Coen et al. |
| 2003/0109869 A1 | 6/2003 | Shadduck |
| 2003/0216792 A1 | 11/2003 | Levin et al. |
| 2004/0147837 A1 | 7/2004 | Macaulay et al. |
| 2004/0147877 A1 | 7/2004 | Heuser |
| 2004/0148019 A1 | 7/2004 | Vidlund et al. |
| 2004/0247849 A1 | 12/2004 | Truckal |
| 2005/0010095 A1 | 1/2005 | Stewart et al. |
| 2005/0015132 A1 | 1/2005 | Kronzon |
| 2005/0203462 A1 | 9/2005 | Katoh et al. |
| 2005/0245923 A1 | 11/2005 | Christopherson et al. |
| 2006/0189972 A1 | 8/2006 | Grossman |
| 2006/0200121 A1 | 9/2006 | Mowery |
| 2006/0224118 A1 | 10/2006 | Morris et al. |
| 2007/0167984 A1 | 7/2007 | Kieval et al. |
| 2007/0208333 A1 | 9/2007 | Uchida et al. |
| 2007/0213704 A1 | 9/2007 | Truckal et al. |
| 2007/0224253 A1 | 9/2007 | Franklin |
| 2008/0114335 A1 | 5/2008 | Flickinger et al. |
| 2008/0125748 A1 | 5/2008 | Patel |
| 2008/0200972 A1 | 8/2008 | Rittman |
| 2009/0036794 A1 | 2/2009 | Stubhaug et al. |
| 2009/0280178 A1 | 11/2009 | Hedge et al. |
| 2010/0152731 A1 | 6/2010 | de la Rama et al. |
| 2010/0168820 A1 | 7/2010 | Maniak et al. |
| 2010/0185087 A1 | 7/2010 | Nields et al. |
| 2010/0241113 A1 | 9/2010 | Ingle |
| 2010/0249702 A1 | 9/2010 | Magana et al. |
| 2010/0286684 A1 | 11/2010 | Hata et al. |
| 2010/0305664 A1 | 12/2010 | Wingeier et al. |
| 2010/0312295 A1 | 12/2010 | Vase et al. |
| 2011/0022127 A1 | 1/2011 | Averina et al. |
| 2011/0028962 A1 | 2/2011 | Werneth et al. |
| 2011/0098761 A1 | 4/2011 | Wittenberger et al. |
| 2011/0144639 A1 | 6/2011 | Govari |
| 2011/0224750 A1 | 9/2011 | Scheiner |
| 2011/0238083 A1 | 9/2011 | Moll et al. |
| 2011/0313417 A1 | 12/2011 | La Rama et al. |
| 2012/0065554 A1 | 3/2012 | Pikus |
| 2012/0089047 A1 | 4/2012 | Ryba et al. |
| 2012/0089123 A1 | 4/2012 | Organ et al. |
| 2012/0116354 A1 | 5/2012 | Heuser |
| 2012/0136350 A1 | 5/2012 | Goshgarian et al. |
| 2012/0143293 A1 | 6/2012 | Mauch et al. |
| 2012/0265198 A1 | 10/2012 | Crow et al. |
| 2012/0271162 A1 | 10/2012 | Liao et al. |
| 2012/0289369 A1 | 11/2012 | Fogarty |
| 2012/0296329 A1 | 11/2012 | Ng |
| 2013/0023758 A1 | 1/2013 | Fabro |
| 2013/0035682 A1 | 2/2013 | Weil |
| 2013/0041257 A1 | 2/2013 | Nemoto |
| 2013/0096550 A1 | 4/2013 | Hill |
| 2013/0103026 A1 | 4/2013 | Kleshinski et al. |
| 2013/0197498 A1* | 8/2013 | Laske ............... A61B 18/1492 606/21 |
| 2013/0226201 A1 | 8/2013 | Miller et al. |
| 2013/0237948 A1 | 9/2013 | Donders et al. |
| 2013/0282000 A1 | 10/2013 | Parsonage et al. |
| 2013/0289369 A1 | 10/2013 | Margolis |
| 2013/0296646 A1 | 11/2013 | Barbut et al. |
| 2013/0304047 A1 | 11/2013 | Grunewald et al. |
| 2013/0310823 A1 | 11/2013 | Gelfand et al. |
| 2013/0331813 A1 | 12/2013 | Barbut et al. |
| 2014/0005706 A1 | 1/2014 | Gelfand et al. |
| 2014/0012251 A1 | 1/2014 | Himmelstein et al. |
| 2014/0025069 A1 | 1/2014 | Willard et al. |
| 2014/0031727 A1 | 1/2014 | Warnking |
| 2014/0058294 A1 | 2/2014 | Gross et al. |
| 2014/0058376 A1 | 2/2014 | Horn et al. |
| 2014/0058377 A1 | 2/2014 | Deem et al. |
| 2014/0067003 A1 | 3/2014 | Vase et al. |
| 2014/0088585 A1 | 3/2014 | Hill et al. |
| 2014/0088588 A1 | 3/2014 | Jarrard |
| 2014/0121641 A1 | 5/2014 | Fischell et al. |
| 2014/0121644 A1 | 5/2014 | Fischell et al. |
| 2014/0180273 A1 | 6/2014 | Nair |
| 2014/0214129 A1 | 7/2014 | Waataja et al. |
| 2014/0276718 A1 | 9/2014 | Turovskiy et al. |
| 2014/0276742 A1 | 9/2014 | Nabutovsky et al. |
| 2014/0303617 A1 | 10/2014 | Shimada |
| 2015/0011834 A1 | 1/2015 | Ayala et al. |
| 2015/0105659 A1 | 4/2015 | Salahieh et al. |
| 2015/0119674 A1 | 4/2015 | Fischell et al. |
| 2015/0141810 A1 | 5/2015 | Weadock |
| 2015/0141985 A1 | 5/2015 | Mayse et al. |
| 2015/0208949 A1 | 7/2015 | Tupin et al. |
| 2015/0223877 A1 | 8/2015 | Behar et al. |
| 2015/0245867 A1 | 9/2015 | Gross |
| 2015/0335286 A1 | 11/2015 | Boydell |
| 2015/0374435 A1 | 12/2015 | Cao et al. |
| 2016/0106499 A1 | 4/2016 | Ogata et al. |
| 2016/0151112 A1 | 6/2016 | Ku et al. |
| 2016/0158554 A1 | 6/2016 | Graig |
| 2016/0163062 A1 | 6/2016 | Garber |
| 2016/0192981 A1 | 7/2016 | Dimmer et al. |
| 2016/0199127 A1 | 7/2016 | Prutchi |
| 2016/0220851 A1 | 8/2016 | Mayse et al. |
| 2016/0242661 A1 | 8/2016 | Fischell et al. |
| 2016/0296171 A1 | 10/2016 | Drori et al. |
| 2016/0317621 A1 | 11/2016 | Bright |
| 2016/0354137 A1 | 12/2016 | Fischell et al. |
| 2016/0374754 A1 | 12/2016 | Asirvatham et al. |
| 2017/0035990 A1 | 2/2017 | Swift |
| 2017/0049989 A1 | 2/2017 | Kapural |
| 2017/0143945 A1 | 5/2017 | Culbert et al. |
| 2017/0202614 A1 | 7/2017 | Gross et al. |
| 2017/0216602 A1 | 8/2017 | Waataja et al. |
| 2017/0231490 A1 | 8/2017 | Toth et al. |
| 2017/0252101 A1 | 9/2017 | Hata et al. |
| 2017/0258522 A1 | 9/2017 | Goshgarian et al. |
| 2018/0036527 A1 | 2/2018 | Reddy et al. |
| 2018/0042669 A1 | 2/2018 | Curley et al. |
| 2018/0178019 A1 | 6/2018 | Reddy et al. |
| 2019/0069942 A1 | 3/2019 | Azamian et al. |
| 2019/0175912 A1 | 6/2019 | Gelfand et al. |
| 2019/0298460 A1 | 10/2019 | Al-Jadda et al. |
| 2019/0343581 A1 | 11/2019 | Panescu et al. |

(56) References Cited

U.S. PATENT DOCUMENTS

| | | | |
|---|---|---|---|
| 2020/0179045 A1* | 6/2020 | Levin | A61B 5/024 |
| 2022/0000545 A1 | 1/2022 | Levin et al. | |
| 2022/0323142 A1 | 10/2022 | Gelfand et al. | |
| 2022/0338924 A1 | 10/2022 | Levin et al. | |
| 2023/0165634 A1 | 6/2023 | Iranitalab et al. | |
| 2023/0380896 A1 | 11/2023 | Panescu et al. | |

FOREIGN PATENT DOCUMENTS

| | | |
|---|---|---|
| CN | 101600471 A | 12/2009 |
| CN | 102670264 A | 9/2012 |
| CN | 102949176 A | 3/2013 |
| CN | 103118619 A | 5/2013 |
| CN | 103220984 A | 7/2013 |
| CN | 103313671 A | 9/2013 |
| CN | 103857353 A | 6/2014 |
| CN | 103908336 A | 7/2014 |
| CN | 104066395 A | 9/2014 |
| CN | 104114220 A | 10/2014 |
| CN | 104257426 A | 1/2015 |
| CN | 104640583 A | 5/2015 |
| EP | 2662027 A1 | 11/2013 |
| EP | 2020943 B1 | 7/2015 |
| EP | 2755588 B1 | 5/2016 |
| EP | 2934357 B1 | 11/2017 |
| EP | 3278825 A2 | 2/2018 |
| JP | 2003526481 A | 9/2003 |
| JP | 2008510530 A | 4/2008 |
| JP | 2009500052 A | 8/2009 |
| JP | 2012030010 A | 2/2012 |
| JP | 2015002920 A | 1/2015 |
| JP | 2015119830 A | 7/2015 |
| JP | 2015536186 A | 12/2015 |
| JP | 2017035519 A | 2/2017 |
| WO | WO99/12489 A2 | 3/1999 |
| WO | WO01/66177 A1 | 9/2001 |
| WO | WO2004/039428 A2 | 5/2004 |
| WO | WO2007/082216 A1 | 7/2007 |
| WO | WO2008/049084 A2 | 4/2008 |
| WO | WO2014/150887 A1 | 9/2014 |
| WO | WO2014/197625 A1 | 12/2014 |
| WO | WO2016/084081 A2 | 6/2016 |
| WO | WO2016/090175 A1 | 6/2016 |
| WO | WO2016/132340 A1 | 8/2016 |
| WO | WO2016/176333 A1 | 11/2016 |
| WO | WO2017/074920 A1 | 5/2017 |
| WO | WO2017/096007 A1 | 6/2017 |
| WO | WO2018/125822 A2 | 7/2018 |
| WO | WO2019/099396 A2 | 5/2019 |
| WO | WO2019/188656 A1 | 10/2019 |
| WO | WO2020/257763 A1 | 12/2020 |

OTHER PUBLICATIONS

Adamopoulos et al; Comparison of different methods for assessing sympathovagal balance in chronic congestive heart failure secondary to coronary artery disease; The American Journal of Cardiology; 70(20); pp. 1576-1582; Dec. 15, 1992.

Andren-Sandberg et al.; Thoracoscopic splanchnicectomy for chronic, severe pancreatic pain; In Seminars in Laparoscopic Surgery; 3(1); Sage CA: Thousand Oaks CA; Sage Publications; pp. 29-33; Mar. 1, 1996.

Baghdadi et al.; Systematic review of the role of thoracoscopic splanchnicectomy in palliating the pain of patients with chronic pancreatitis; Surgical endoscopy; 22(3); pp. 580-588; Dec. 28, 2007.

Barnes et al.; Haemodynamic responses to stimulation of the splanchnic and cardiac sympathetic nerves in the anaesthetized cat; The Journal of Physiology; 378; pp. 417-436; Sep. 1986.

Bauereisen et al.; The Importance of mesenteric mechanoreceptors for the reflex innervation of resistance blood vessels capacity blood vessels in the splanchnic area; Pflugers Archiv fur die gesamte Physiologie des Menschen und der Tiere; 276; pp. 445-455; Jan. 1963.

Bradley et al.; Nerve blocks and neuroablative surgery for chronic pancreatitis; World J. Surg.; 27(11); pp. 1241-1248; Nov. 1, 2003.

Brooksby et al.; Dynamic changes in splanchnic blood flow and blood volume in dogs during activation of sympathetic nerves; Circulation Research; XXIX(3); pp. 227-238; Sep. 1971.

Brunner et al.; Carotid sinus baroreceptor control of splanchnic resistance and capacity. Am J Physiol.; 255; pp. H1305-1310; Dec. 1988.

Burchell et al.; Chemohypersensitivity and autonomic modulation of venous capacitance in the pathophysiology of acute decompensated heart failure; Current Heart failure Reports; 10(2); pp. 139-146; Jan. 2013.

Burkhoff et al.; Why does pulmonary venous pressure rise after on of LV dysfunction: a theoretical analysis; Am. J. Physiol.; 265(5, pt. 2); pp. H1819-1828; Nov. 1993.

Buscher et al.; Bilateral thoracoscopic splanchnicectomy for pain in patients with chronic pancreatitis impairs adrenomedullary but not noradrenergic sympathetic function; Surgical Endoscopy; 26(8); p. 2183-2188; Aug. 2012.

Buscher et al.; Limited effect of thoracoscopic splanchnicectomy in the treatment of severe chronic pancreatitis pain: a prospective long-term analysis of 75 cases; Surgery; 143(6); pp. 715-722; Jun. 30, 2008.

Carneiro et al.; Change in liver blood flow and blood content in dogs during direct and reflex alteration of hepatic sympathetic nerve activity; Circulation Research; 40(2); pp. 150-158; Feb. 1, 1977.

Chatterjee et al.; Novel interventional therapies to modulate the autonomic tone in heart failure; JACC: Heart Failure; 3(10); pp. 786-802; Oct. 2015.

Cody et al.; Captopril kinetics in chronic congestive heart failure; Clin pharmacol Ther.; 32(6); pp. 721-726; Dec. 1982.

Crespy et al.; Anatomical bases of the transhiatus approach to the greater splanchnic nerve; Anatomia Clinica; 6(4); pp. 247-254; Dec. 1, 1984.

Cuschieri et al.; Bilateral endoscopic splanchnicectomy through a posterior thoracoscopic approach; Journal of the Royal College of Surgeons of Edinburgh; 39(1); pp. 44-47; Feb. 1994.

Dayal et al.; Variations in the formation of thoracic splanchnic nerves; European Journal of Anatomy; vol. 18; pp. 141-151; 2014 (the year of publication is sufficiently earlier than the effective U.S. filing date and any foreign priority date so that the particular month of publication is not in issue).

Del Rio et al.; Carotid chemoreceptor ablation improves survival in heart failure: rescuing autonomic control of cardiorespiratory function; Journal of the American College of Cardiology; 62(25); pp. 2422-2430; Dec. 24, 2013.

Diedrich et al.; Segmental orthostatic fluid shifts; Clinical autonomic research; 14(3); pp. 146-147; Jun. 2004.

Edwards LifeSciences; ClearSight System (brochure; No. AR11578); 4 pgs.; © 2014 (the year of publication is sufficiently earlier than the effective U.S. filing date and any foreign priority date so that the particular month of publication is not in issue).

Edwards; The glycogenolytic response to stimulation of the splanchnic nerves in adrenalectomized calves, sheep, dogs, cats and pigs; J Physiol.; 213, pp. 741-759; Mar. 1971.

Eisenberg et al.; Neurolytic celiac plexus block for treatment of cancer pain: A meta-analysis; Anesth Analg; 80(2); pp. 290-295; Feb. 1995.

Fallick et al.; Sympathetically mediated changes in capacitance: Redistribution of the venous reservoir as a cause of decompensation; Circulation: Heart Failure; 4; pp. 669-675; Sep. 2011.

Ferrara et al.; Hemodynamics of the splanchnic and systemic circulation after hypotonic water load-comparison between normal subjects and patients with congestive heart failure; Acta Cardiologica; 38(2); pp. 81-88; Dec. 1982.

Fiaccadori et al.; Ultrafiltration in Heart Failure; Am Heart J.; 161(3); pp. 439-449; Mar. 2011.

Folkow et al.; The Effect of Graded Vasoconstrictor Fibre Stimulation on the Intestinal Resistance and Capacitance Vessels; Acta physiologica Scandinavica; 61; pp. 445-457; Aug. 1964.

(56) References Cited

OTHER PUBLICATIONS

Foss et al.; Reversal of genetic salt-sensitive hypertension by targeted sympathetic ablation; Hypertension; 61(4); pp. 806-811; Apr. 1, 2013.
Francis et al.; Clinical notes, suggestions and new instrument; JAMA; 134(1); pp. 20-21; May 3, 1947.
Fudim et al.; Role of volume redistribution in the congestion of heart failure; Journal of the American Heart Association; 6(8); e006817; 11 pages; Aug. 1, 2017.
Fujita; Splanchnic circulation following coeliac plexus block; Acta Anaesthesiol Scand.; 32(4); pp. 323-327; May 1988.
Gafanovich et al.; Chronic diarrhea-induced by celiac plexus block?; Journal of Clinical Gastroenterology; 26(4); pp. 300-302; Jun. 1, 1998.
Gambro®; Aquadex FlexFlowTM (brochure, No. L5189 Rev. B); 4 pgs.; © Aug. 2011.
Garcea et al.; Percutaneous splanchnic nerve radiofrequency ablation for chronic abdominal pain; ANZ Journal of Surgery; 75(8); pp. 640-644; Aug. 1, 2005.
Giraudo et al.; Endoscopic palliative treatment of advanced pancreatic cancer: Thoracoscopic splanchnicectomy and laparoscopic gastrojejunostomy; Annals of Oncology; 10(4); pp. S278-S280; Jan. 1, 1999.
Girouard et al.; Optical mapping in a new guinea pig model of ventricular tachycardia reveals mechanisms for multiple wavelengths in a single reentrant circuit; Circulation; 93(3); pp. 603-613; Feb. 1, 1996.
Goldblatt et al.; Studies on experimental hypertension II: The effect of resection of splanchnic nerves on experimental renal hypertension; The Journal of Experimental Medicine; 65(2); pp. 233-241; Feb. 1, 1937.
Goroszeniuk et al.; Permanent percutaneous splanchnic nerve neuromodulation for management of pain due to chronic pancreatitis: A case report; Neuromodulation; ;14(3); pp. 253-257; May-Jun. 2011.
Greenway et al.; Role of splanchnic venous system in overall cardiovascular homeostasis; In Federal Proceedings; 42(6); pp. 1678-1684; Apr. 1983.
Greenway; Blockade of reflex venous capacitance responses in liver and spleen by hexamethonium, atropine, and surgical section; Can. J. Physiol. Pharmacol.; 69(9): 1284-1287; Sep. 1991.
Griffith et al.; The vasomotor control of the liver circulation; American Journal of Physiology; 95(1); pp. 20-34; Oct. 1930.
Griffith et al.; Vasomotor Control of the Liver Circulation. Proceedings of the Society for Experimental Biology and Medicine; 27(7); pp. 673-674; Apr. 1930.
Herman et al.; Splenic afferents and some of their reflex responses; American Journal of Physiology-Regulatory, Integrative and Comparative Physiology; 242(3); pp. R247-R254; Mar. 1982.
Ihse et al.; Bilateral thoracoscopic splanchnicectomy: effects on pancreatic pain and function; Annals of Surgery; 230(6); pp. 785-791; Dec. 1, 1999.
Ischia et al.; A new approach to the neurolytic block of the coeliac plexus: the transaortic technique; Pain; 16(4); pp. 333-341; Aug. 31, 1983.
Johnson et al.; An open randomized comparison of clinical effectiveness of protocol-driven opioid analgesia, celiac plexus block or thoracoscopic splanchnicectomy for pain management in patients with pancreatic and other abdominal malignancies; Pancreatology; 9(6); pp. 755-763; Jan. 1, 2009.
Kang et al.; Bilateral thoracoscopic splanchnicectomy with sympathectomy for managing abdominal pain in cancer patients; Am J Surg; 194(1); pp. 23-29; Jul. 2007.
Kapural et al.; Splanchnic block at T11 provides a longer relief than celiac plexus block from nonmalignant, chronic abdominal pain; Pain management; 9(2); pp. 115-121; Mar. 2019.
Katri et al.; Thoracoscopic splanchnicectomy for pain control in irresectable pancreatic cancer; Journal of Laparoendoscopic and Advanced Surgical Techniques; 18(2); pp. 199-203; Apr. 1, 2008.
Kaufman et al.; Effect of portal hypertension on splenic blood flow, intrasplenic extravasation and systemic blood pressure; American Journal of Physiology—Regulatory, Integrative and Comparative Physiology; 284(6); pp. R1580-1585; Jun. 1, 2003.
Kimura et al.; Application of electrical impedance analysis for diagnosis of a pulmonary mass; Chest; 105(6); pp. 1679-1682; Jun. 1994.
King et al.; Splanchnic circulation is a critical neural target in angiotensin II salt hypertension in rats; Hypertension; 50(3); pp. 547-556; Sep. 2007.
Koutsouflianiotis et al.; A left-sided azygos vein in a cadaver: anatomical and surgical considerations; Cureus Journal of Medical Science; 10(5); 4 pages; May 10, 2018.
Krishna et al.; Video-assisted thoracoscopic sympathectomy-splanchnicectomy for pancreatic cancer pain; Journal of Pain and Symptom Management; 22(1); pp. 610-616; Jul. 1, 2001.
Lang-Lazdunski et al.; Videothoracoscopic splanchnicectomy for intractable pain from adrenal metastasis; Ann Thorac Surg; 73(4); pp. 1290-1292; Apr. 2002.
Le Pimpec Barthes; Thoracoscopic splanchnicectomy for control of intractable pain in pancreatic cancer; The Annals of Thoracic Surgery; 65(3); pp. 810-813; Mar. 31, 1998.
Leksowski; Thoracoscopic splanchnicectomy for the relief of pain due to chronic pancreatitis; Surg Endosc., 15(6); pp. 592-596; Jun. 2001.
Lica et al.; Thoracoscopic left splanchnicectomy—role in pain control in unresectable pancreatic cancer. Initial experience; Chirurgia; 109(3); pp. 313-317; May-Jun. 2014.
Lieberman et al.; Celiac plexus neurolysis with the modified transaortic approach; Radiology; 175(1); pp. 274-276; Apr. 1990.
Lillemoe et al.; Chemical splanchnicectomy in patients with unresectable pancreatic cancer. A prospective randomized trial; Annals of Surgery; 217(5); pp. 447-457; May 1, 1993.
Lin et al.; Bilateral thoracoscopic lower sympathetic-splanchnicectomy for upper abdominal cancer pain. The European journal of surgery; Supplement 572; pp. 59-62; 1994 (the year of publication is sufficiently earlier than the effective U.S. filing date and any foreign priority date so that the particular month of publication is not in issue).
Lonroth et al.; Unilateral left-side thoracoscopic sympathectomy for visceral pain control: a pilot study; The European Journal of Surgery; 163(2); pp. 97-100; Feb. 1, 1997.
Loukas et al.; A review of the thoracic splanchnic nerves and celiac ganglia; Clinical Anatomy; 23(5); pp. 512-522; Jul. 2010.
Maass-Moreno et al.; Carotid baroreceptor control of liver and spleen volume in cats; Am J Physiol; 260(1 Pt 2); pp. H254-259; Jan. 1991.
Maher et al.; Thoracoscopic splanchnicectomy for chronic pancreatitis pain; Surgery; 120(4); pp. 603-610; Oct. 1996.
Mallet-Guy et al.; Treatment of chronic pancreatitis by unilateral splanchnicectomy; Archives of Surgery; 60(2); pp. 233-241; Feb. 1, 1950.
Masuda et al.; Splanchnicectomy for pancreatic cancer pain; BioMed Research International; Jan. 1, 2014.
Myhre et al.; Monitoring of celiac plexus block in chronic pancreatitis; Pain; 38(3); pp. 269-274; Sep. 1989.
Naidoo et al.; Thoracic splanchnic nerves: implications for splanchnic denervation; Journal of Anatomy; 199(5); pp. 585-590; Nov. 2001.
Nakazato et al.; Extrinsic innervation of the canine abdominal vena cava and the origin of cholinergic vasoconstrictor nerves; J. Physiol.; 328; pp. 191-203; Jul. 1982.
Nath et al.; Biophysics and pathology of catheter energy delivery systems; Progress in Cardiovascular Diseases; XXXVII(4); pp. 185-204; Jan./Feb. 1995.
Norman: Posterior Mediastinum; As last known Jun. 6, 2013; retrieved from the internet (https: web.archive.org/web/20130606053828/http://www.wesnorman.com/thoraxlesson5.htm); 11 pages; on Sep. 16, 2020.
Pan et al.; Differential responses of regional sympathetic activity and blood flow to visceral afferent stimulation; Am J Physiol Regul Integr Comp Physiol.; 280(6); pp. R1781-1789; Jun. 2001.

(56) References Cited

OTHER PUBLICATIONS

Piciucchi et al.; The azygos vein pathway: an overview from anatomical variations of pathological changes; Insights Imaging; 5(5); pp. 619-628; Oct. 2014.

Pietrabissa et al.; Thoracoscopic splanchnicectomy for pain relief in unresectable pancreatic cancer; Archives of Surgery: 135(3); pp. 332-335; Mar. 1, 2000.

Plancarte et al.; Management of chronic upper abdominal pain in cancer: transdiscal blockage of the splanchnic nerves; Regional Anesthesia and Pain Medicine; 35(6); pp. 500-506; Nov. 1, 2010.

Prasad et al.; Thoracoscopic splanchinicectomy as a palliative procedure for pain relief in carcinoma pancreas; Journal of Minimal Access Surgery; 5(2); pp. 37-39; (Author Manuscript); Apr. 1, 2009.

Puntawangkoon et al.; Reduced peripheral arterial blood flow with preserved cardiac output during submaximal bicycle exercise in elderly heart failure; Journal of Cardiovascular Magnetic Resonance; 11(1); pp. 1-11; Dec. 2009.

Raj; Celiac plexus/splanchnic nerve blocks; Techniques in Regional Anesthesia and Pain Management; 5(3); pp. 102-115; Jul. 2001.

Raj et al.; Radiofrequency lesioning of splanchnic nerves; Pain Practice; 2(3); pp. 242-247; Sep. 2002.

Raj et al.; The development of a technique for radiofrequency lesioning of splanchnic nerves; Current Review of Pain; 3(5); pp. 377-387; Oct. 1999.

Sadar et al.; Bilateral thoracic sympathectomy-splanchnicectomy in the treatment of intractable pain due to pancreatic carcinoma; Cleveland Clinic Quarterly; 41; pp. 185-188; 1974 (the year of publication is sufficiently earlier than the effective U.S. filing date and any foreign priority date so that the particular month of publication is not in issue).

Saenz et al.; Thoracoscopic splanchicectomy for pain control in patients with unresectable carcinoma of the pancreas; Surgical Endoscopy; 14(8); pp. 717-720; Aug. 1, 2000.

Sastre et al.; Transhiatal bilateral splanchnicotomy for pain control in pancreatic cancer: basic anatomy, surgical technique, and immediate results in fifty-one cases; Surgery; 111(6); pp. 640-646; Jun. 1992.

Scott-Douglas et al.; Effects of acute volume loading and hemorrhage on intestinal vascular capacitance: a mechanism whereby capacitance modulates cardiac output; Can. J. Cardiol.; 18(5); pp. 515-522; May 5, 2002.

Shimada et al.; Clinical evaluation of transhiatal bilateral splanchnicotomy for patients with intractable supramesenteric pain; Surgery Today; 29(11); pp. 1136-1140; Nov. 1999.

Smigielski et al.; Assessment of quality of life in patients with non-operated pancreatic cancer after videothoracoscopic splanchnicectomy; Videosurgery and Other Miniinvasive Techniques; 6(3); pp. 132-137; Sep. 1, 2011.

Stefaniak et al.; A comparison of two invasive techniques in the management of intractable pain due to inoperable pancreatic cancer; European Journal of Surgical Oncology; 31(7); pp. 768-773; Sep. 30, 2005.

Takahashi et al.; Thoracoscopic splanchnicectomy for the relief of intractable pain; Surgical Endoscopy: 10(1); pp. 65-68; Jan. 1, 1996.

Tavassoli et al.; Thoracoscopic splanchnicectomy for pain control in urresectable pancreatic cancer; Journal of Cardio-Thoracic Medicine; 1(2); pp. 53-56; Aug. 6, 2013.

Triposkiadis et al.; The sympathetic nervous system in heart failure: physiology, pathophysiology, and clinical implications; Journal of the American College of Cardiology; 54(19); pp. 1747-1762; Nov. 3, 2009.

Tsybenko et al.; Central nervous control of hepatic circulation; J Aut Nerv Sys; 33(3); pp. 255-266; May 1991.

Van Vliet et al.; Time course of renal responses to greater splanchnic nerve stimulation; American Journal of Physiology Regulatory, Integrative and Comparative Physiology; 260(5); pp. R894-R905; May 1991.

Verhaegh et al.; Percutaneous radiofrequency ablation of the splanchnic nerves with chronic pancreatitis: results of single and repeated procedures in 11 patients; Pain Practice; 13(8); pp. 621-626; (Author Manuscript); Nov. 1, 2013.

Wilkins et al.; The effect of splanchnic sympathectomy in hypertensive patients upon estimated hepatic blood flow in the upright as contrasted with the horizontal position; Journal of Clinical Investigation; 30(3); pp. 312-317; Mar. 1951.

Worsey et al.; Thoracoscopic pancreatic denervation for pain control in irrsectable pancreatic cancer; British Journal of Surgery; 80(8); pp. 1051-1052; Aug. 1, 1993.

Wroclaw Medical Univ. (Poland); Removing a section of nerve visceral improved (press release; with machine translation); retrieved Oct. 10, 2016 from the internet: http://www.zdrowie.abc.com pi/aktualnosci/wroclaw-usunicie-fragmentu-nerwu-trzewnego-poprawiio-u-chorej-wydolnosc-serca,25247 html; 5 pgs.; Sep. 23, 2016.

Yan et al.; Neurolytic celiac plexus block for pain control in unresectable pancreatic cancer; Am J Gastroenterol; 102(2); pp. 430-438; Feb. 2007.

Levin et al.; U.S. Appl. No. 15/017,260 entitled "Devices and Methods for Treatment of Heart Failure by Splanchnic Nerve Ablation," filed Feb. 5, 2016.

Gelfand et al.; U.S. Appl. No. 18/171,972 entitled "Devices and methods for treatment of heart failure via electrical modulation of a splanchnic nerve," filed Feb. 21, 2023.

Panescu et al.; U.S. Appl. No. 18/332,599 entitled "Methods and devices for endovascular ablation of a splanchnic nerve," filed Jun. 9, 2023.

\* cited by examiner

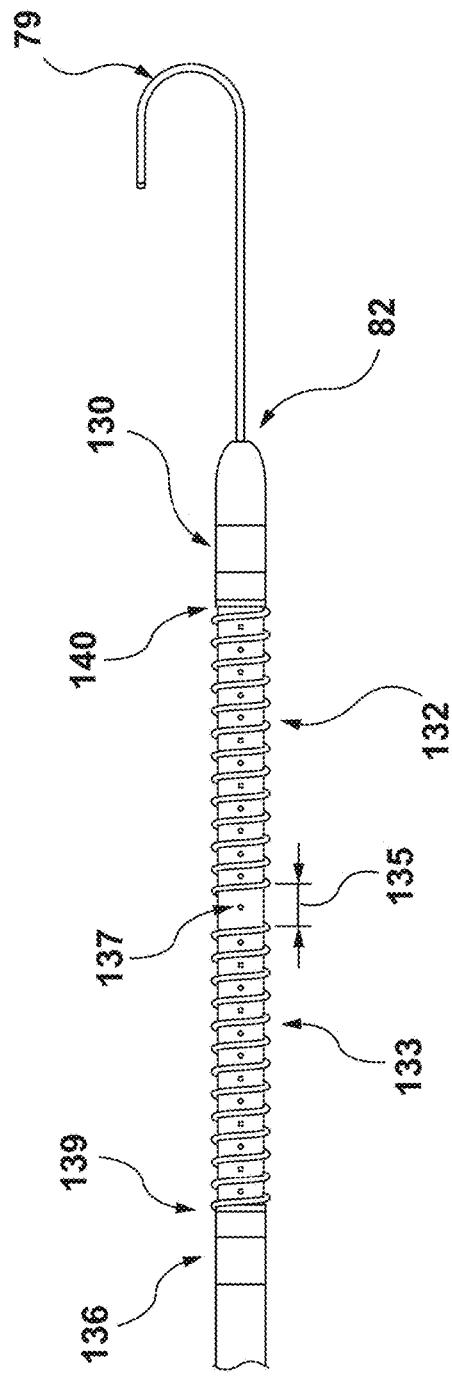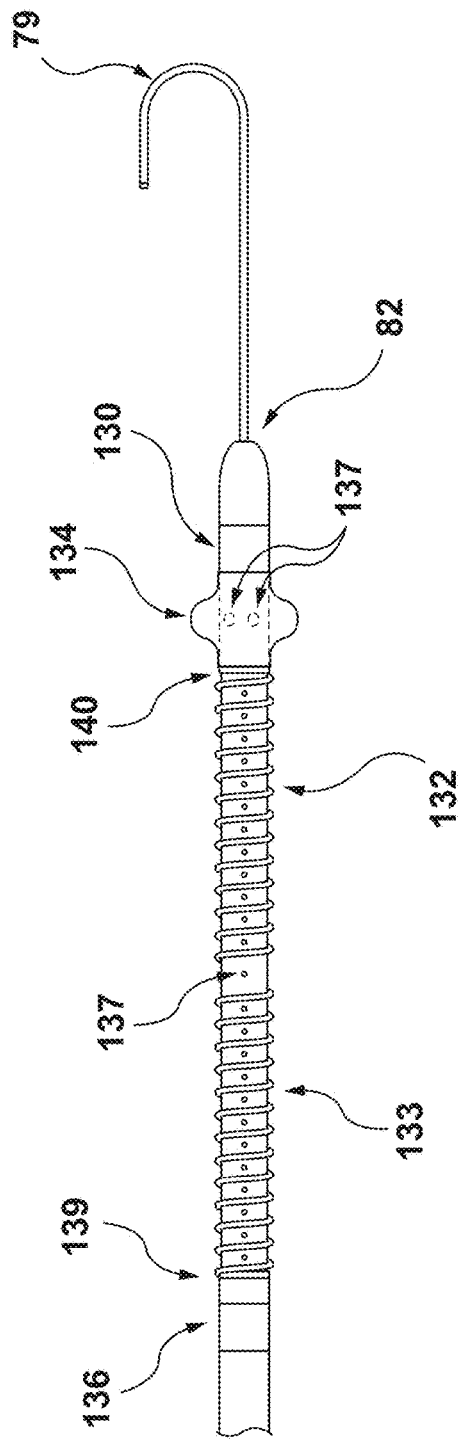

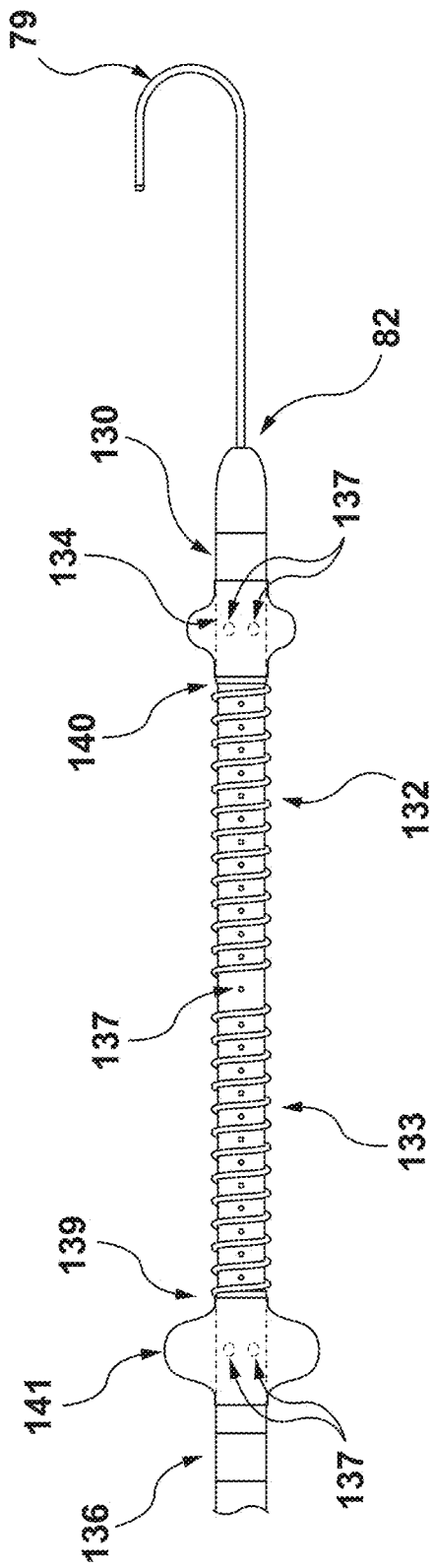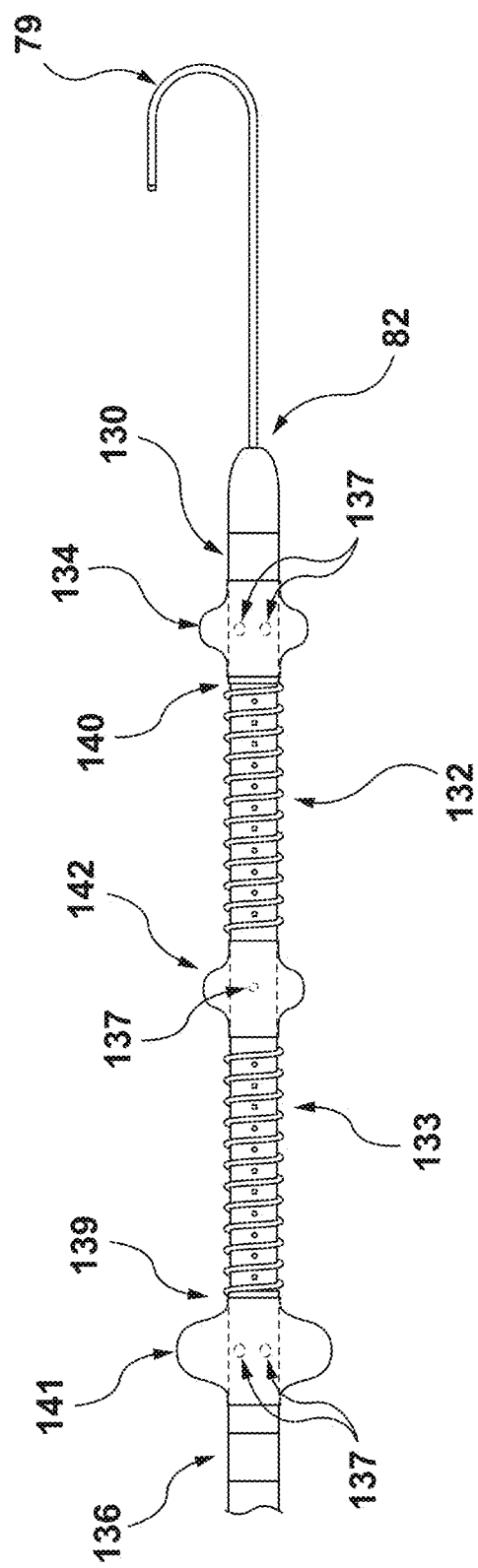

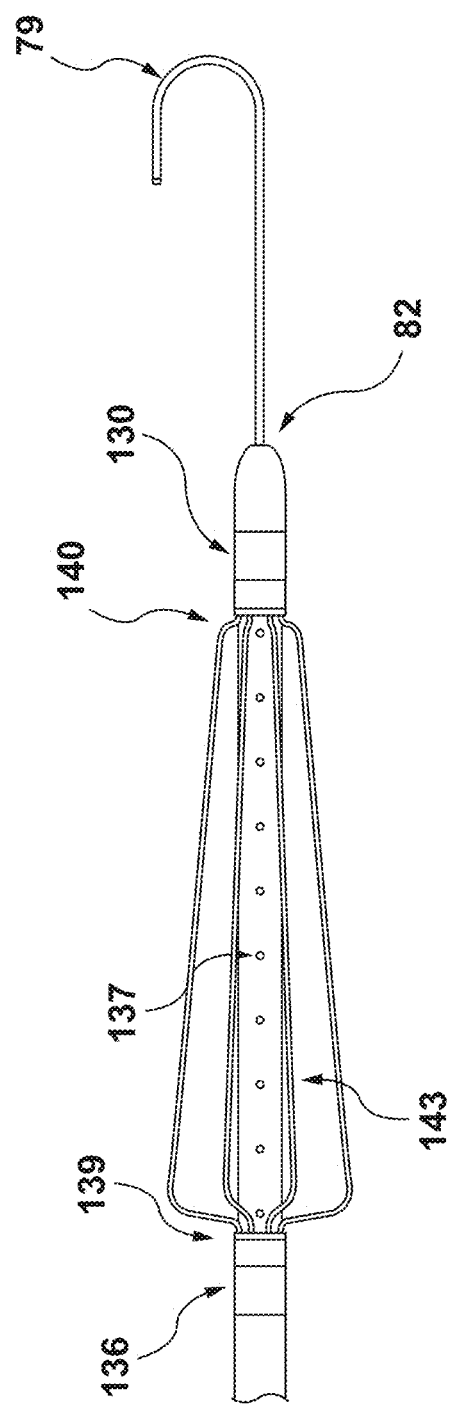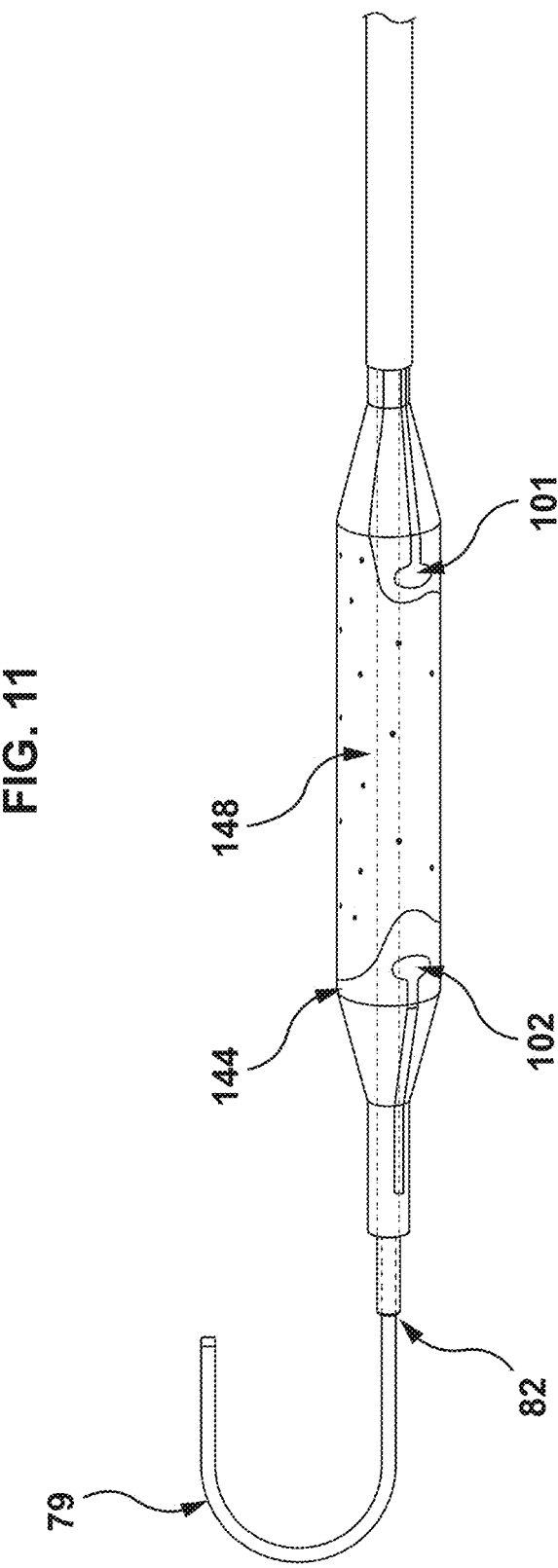

METHODS AND DEVICES FOR ENDOVASCULAR ABLATION OF A SPLANCHNIC NERVE

INCORPORATION BY REFERENCE

This application is a continuation of U.S. application Ser. No. 17/451,991, filed Oct. 22, 2021, which is a continuation of International Application No. PCT/US2020/038934, filed Jun. 22, 2020, which claims the benefit of U.S. Provisional Application No. 62/864,093, filed Jun. 20, 2019 and U.S. Provisional Application No. 62/881,251, filed Jul. 31, 2019, the disclosures of which are incorporated by reference herein in their entireties for all purposes.

All publications and patent applications mentioned in this specification are herein incorporated by reference to the same extent as if each individual publication or patent application was specifically and individually indicated to be incorporated by reference.

This disclosure is related by subject matter to the disclosure in U.S. Pub. Nos. US2019/0175912, US2019/0183569, U.S. Pat. Nos. 10,376,308, 10,207,110, U.S. application Ser. Nos. 16/510,503, 62/836,720, 62/837,090, 62/864,093, PCT/US2019/15400 and PCT Pub. No. WO2018/023132, WO2019/118976, all of which are incorporated herein by reference in their entirety for all purposes.

BACKGROUND

Heart failure (HF) is a medical condition that occurs when the heart is unable to pump sufficiently to sustain the organs of the body. Heart failure is a serious condition and affects millions of patients in the United States and around the world.

One common measure of heart health is left ventricular ejection fraction (LVEF) or ejection fraction. By definition, the volume of blood within a ventricle immediately before a contraction is known as the end-diastolic volume (EDV). Likewise, the volume of blood left in a ventricle at the end of contraction is end-systolic volume (ESV). The difference between EDV and ESV is stroke volume (SV). SV describes the volume of blood ejected from the right and left ventricles with each heartbeat. Ejection fraction (EF) is the fraction of the EDV that is ejected with each beat; that is, it is SV divided by EDV. Cardiac output (CO) is defined as the volume of blood pumped per minute by each ventricle of the heart. CO is equal to SV times the heart rate (HR).

Cardiomyopathy, in which the heart muscle becomes weakened, stretched, or exhibits other structural problems, can be further categorized into systolic and diastolic dysfunction based on ventricular ejection fraction.

While a number of drug therapies successfully target systolic dysfunction and HFrEF, for the large group of patients with diastolic dysfunction and HFpEF no promising therapies have yet been identified. The clinical course for patients with both HFrEF and HFpEF is significant for recurrent presentations of acute decompensated heart failure (ADHF) with symptoms of dyspnea, decreased exercise capacity, peripheral edema, etc. Recurrent admissions for ADHF utilize a large part of current health care resources and could continue to generate enormous costs.

While the pathophysiology of HF is becoming increasingly better understood, modern medicine has, thus far, failed to develop new therapies for chronic management of HF or recurrent ADHF episodes. Over the past few decades, strategies of ADHF management and prevention have and continue to focus on the classical paradigm that salt and fluid retention is the cause of intravascular fluid expansion and cardiac decompensation.

Thus, there remains a need for improved therapies for heart failure patients that are safe and effective, and devices and systems that are adapted and configured to perform those therapies.

SUMMARY OF THE DISCLOSURE

The disclosure is related to methods of, devices for, and approaches for ablating a thoracic splanchnic nerve or a thoracic splanchnic nerve root. The ablations can be performed to treat at least one of hypertension and heart failure, but the general methods may also be used for other treatments as well. For example, the methods herein can be used in the treatment of pain, or even to generally benefit the subject to reducing the amount of blood that is expelled from the splanchnic bed into the central thoracic veins.

The treatments herein may be accomplished by increasing splanchnic capacitance. The therapies generally include ablating a patient's preganglionic thoracic splanchnic nerve or thoracic splanchnic nerve root to increase splanchnic capacitance, and thereby treat at least one of hypertension and heart failure.

Methods herein describe ablating thoracic splanchnic nerves, such as a greater splanchnic nerve or greater splanchnic nerve roots. While methods herein may provide specific examples of targeting greater splanchnic nerve or greater splanchnic nerve roots, it may be possible to alternatively, or in addition to, ablate other thoracic splanchnic nerves (e.g., lesser, least) to perform one or more treatments herein.

One aspect of the disclosure is a method of ablating tissue by positioning a medical device intravascularly in the vicinity of target tissue, and using the medical device to ablate tissue and create a lesion. One aspect of the disclosure a method of ablating tissue by positioning a medical device intravascularly into one or more target vessels, and using the medical device to ablate tissue and create a lesion. The methods herein can thus be described as methods that position a medical device near target tissue to be ablated and/or methods that position a medical device in one or more vessels, where the target tissue is relatively near to the target regions within the one or more vessels. Any of the method steps herein (including, for example without limitation, in the claims or the Description section) can be incorporated into any other method of use herein unless specifically indicated to the contrary herein.

One aspect of the disclosure is a method of ablating a greater splanchnic nerve or a greater splanchnic nerve root to increase splanchnic venous blood capacitance and/or venous compliance, the method including advancing a medical device into a first vessel, advancing the medical device at least partially into a second vessel, and delivering ablation energy from the medical device to create a lesion in tissue surrounding the first vessel.

In some embodiments the first vessel is an azygos vein and the second vessel is an intercostal vein. The intercostal vein may be one of the three lowest intercostal veins. The intercostal vein may be a T9, T10, or T11 intercostal vein.

The methods may include positioning a distal end of an ablation element in the second vessel and no more than 30 mm (e.g., 20 mm, 15 mm, 12 mm) from a junction between the first vessel and the second vessel when delivering the energy from the ablation element.

The methods may include a proximal portion of an ablation element being disposed in the second vessel when delivering energy.

The methods may include aligning or positioning the ablation element with respect to a boney landmark, such as a costovertebral joint at the same vertebral level at which the second vessel (e.g., intercostal vein) resides.

In some embodiments aligning or positioning the ablation element with respect to a boney landmark, such as a costovertebral joint, includes viewing the boney landmark with medical imaging such as fluoroscopy.

In some embodiments viewing the boney landmark with medical imaging such as fluoroscopy includes orienting the medical imaging perspective at an anterior oblique angle in a range of 25° to 65° from AP (e.g., in a range of 30° to 60°, in a range of 35° to 55°) toward the side of the patient where the target nerve resides.

In some embodiments viewing the boney landmark with medical imaging such as fluoroscopy includes orienting the medical imaging perspective approximately perpendicular to a line between the patient's first vessel (e.g., azygos vein) and the boney landmark (e.g., costovertebral joint).

In some embodiments aligning the ablation element with respect to a boney landmark includes aligning a radiopaque marker positioned on the catheter element containing the ablation element with the boney landmark.

The method may include creating a lesion at a distance of 5 mm around the ablation element. Creating a lesion may include ablating a portion of a thoracic splanchnic nerve or a thoracic splanchnic nerve root, e.g., a greater splanchnic nerve or GSN root. A lesion may be a continuous lesion. The lesion may have a length from 5 mm to 25 mm, such as 10 mm to 25 mm, such as 15 mm to 20 mm. A lesion may be a circumferential lesion all the way around the second vessel. The lesion may, however, be less than circumferential all the way around the second vessel, such as 225 degrees or less, 180 degrees or less, 135 degrees or less, 90 degrees or less, 45 degrees or less.

The methods may include positioning an entire ablation element in the second vessel, while the method can also include positioning less than the entire length of the ablation element in the second vessel.

The methods may include performing an ablation process from within more than one target vessel, such as an intercostal vein or an azygos vein. The methods of ablation herein may also be performed in the second vessel.

The methods may include performing an ablation confirmation test, such as any of the tests herein. If desired or needed, an ablation element may be repositioned into a second target vessel, which may be an azygos vein or a different intercostal vein.

The methods can also include, prior to, during, and/or subsequent to delivering the ablation energy, delivering stimulation energy to first and second stimulation electrodes carried by the medical device. Delivering stimulation energy may help determine if the ablation element is in a target location within the intercostal vein, and/or if an ablation procedure was effective.

One aspect of the disclosure is a method that includes delivering an ablation catheter comprising an energy delivery element (or member) through a venous system of the patient, positioning the energy delivery element at least partially (optionally completely) inside a vein selected from T9, T10 and T11 intercostal veins, delivering ablation energy from the energy delivery element to create a continuous lesion having a depth of at least 5 mm and a length from 10 to 25 mm. The continuous lesion and its parameters can be formed by selecting or choosing certain energy delivery parameters that will create the lesion. In some embodiments, the lesion can extend from an ostium of an azygos vein to up to 20 mm along the intercostal vein. Any of the other method steps herein that are described in the context of other methods can be performed with this exemplary method.

In some alternative methods herein, a plurality of ablations (i.e., from ablation energy on to energy ablation off) can be performed within a single target vessel (e.g., an intercostal vein) to create a total lesion made from two or more lesions made from the plurality of ablations. The total lesion made from the plurality of lesions can have any of characteristics of the other lesions herein. For example, the total lesion can be continuous (made by the connection of a plurality of lesions created during different ablations), may be up to 20 mm long, can be circumferential (or not), etc. After a first ablation, the ablation device can be moved within the same vessel and create a second lesion, which may or may not overlap with a first lesion. This can be repeated as many times as desired. Any of the stimulation or testing steps herein can be performed before, during, or after any ablation step, even if a plurality of ablations are performed in a single vessel.

One aspect of the disclosure is a method of positioning an ablation catheter in a T9, T10, or T11 intercostal vein in a position for ablating a greater splanchnic nerve (GSN), the method including imaging a portion of a subject, the portion including at least one of a T9, T10, or T11 intercostal vein and a portion of the subject's spine: positioning a distal section of an ablation catheter in the T9, T10, or T11 intercostal vein; and positioning an ablation catheter radiopaque marker at a location based on the position of the radiopaque marker relative to an anatomical landmark, such as one or more of a portion of the spine, a rib, a costovertebral joint, an azygous vein, or an ostium between the azygous vein and the T9, T10, or T11 intercostal vein. The method may further include delivering energy from an ablation catheter ablation element to ablate tissue.

One aspect of the disclosure is a method that includes characterizing a relative position of a patient's azygos vein to determine if the azygos is centered or substantially centered, right-biased (to the patient's right of center), or left-biased (to the patient's left of center). The characterization step may occur while viewing a particular portion of the patient's anatomy, and from a particular viewpoint that allows the characterization to accurately take place. The method may further include positioning an ablation catheter based on the characterization step.

One aspect of this disclosure is a method of characterizing the position of a human patient's azygos vein relative to a portion of the patient's spine, comprising: imaging at least a portion of the patient's spine and vasculature, in particular the azygos vein and/or one or more intercostal veins, using an imaging device, in particular using a radiographic imaging device with a radiopaque contrast agent injected into the patient's vasculature, or imaging at least one radiopaque device, positioned in the azygos vein and/or in one or more intercostal veins, relative to a portion of the spine, using an imaging device, in particular using a radiographic imaging device, to thereby characterize the position of the patient's azygos vein relative to a midline of the spine, the radiopaque device optionally comprising a radiopaque portion of a guidewire; and determining if the azygos vein is centered, left-biased or right biased with respect to the midline of the vertebra based on one or more images generated by said imaging device. This aspect may further include a method of determining a proper position where a catheter should be inserted in a vasculature of a human patient, in particular in order to allow ablating a greater splanchnic nerve or greater splanchnic nerve roots, the method comprising determining where to place an ablation element of a catheter for transvascular ablation, in particular any of the ablation catheters herein, based on said determination of if the azygos vein is centered, left-biased or right biased with respect to the midline of the vertebra.

This aspect may further comprise determining where to place a radiopaque marker carried by the distal section of an ablation catheter, optionally a proximal radiopaque marker positioned proximal to any ablation element carried by the same distal section, based on said determination of if the azygos vein is centered, left-biased or right biased with respect to the midline of the vertebra.

One aspect of the disclosure is a method of determining proper positioning of a catheter inserted in a vasculature of a human patient, optionally of a catheter according to any of the claims or disclosure herein, wherein the catheter comprises an elongate shaft with a distal section carrying one or more ablation elements and a proximal radiopaque marker, with the distal section of the elongate shaft positioned in a T9, T10, or T11 intercostal vein; wherein the method comprises: determining if the azygos vein is centered, left-biased or right biased with respect to the midline of the vertebra, assessing the position of the proximal radiopaque marker relative to the midline of the vertebra, verifying if the catheter is properly positioned relative to a patient's anatomical landmark, wherein verifying comprises: considering that the catheter is properly positioned when one of the following circumstances takes place: if the azygos vein is right-biased, the proximal radiopaque marker is placed at the ostium of the intercostal vein, to the right of midline of the vertebra, if the azygos vein is centered or left-biased, the proximal radiopaque marker is aligned with the midline of the vertebra.

In any of the method aspects herein, the proximal radiopaque marker may be carried by the distal section and may be positioned proximal to all the ablation element(s). The proximal radiopaque marker may be positioned directly proximal to the ablation element or directly proximal to the most proximal of the ablation elements carried by the distal section of the catheter.

In any of the method aspects herein, the catheter may comprise a distal radiopaque marker positioned distal to all the ablation element(s) and wherein the step of verifying also includes: assessing the position of the distal radiopaque marker relative to the patient's costovertebral joint and/or rib, ascertaining that the distal radiopaque marker is spaced from the costovertebral joint and/or rib at least a prefixed threshold distance. The distal radiopaque marker may be positioned directly distal to the ablation element, or directly distal to the most distal of the ablation elements carried by the distal region of the catheter, and wherein ascertaining comprises ascertaining that the distal radiopaque marker is at least 3 mm, preferably at least 5 mm, far from the costovertebral joint.

In any of the method aspects herein, verifying may comprise considering that the catheter is not properly positioned when none of the following circumstances takes place: if the azygos vein is right-biased, the proximal radiopaque marker is placed at the ostium of the intercostal vein, to the right of midline of the vertebra, if the azygos vein is centered or left-biased, the proximal radiopaque marker is aligned with the midline of the vertebra.

In any of the method aspects herein, if it has been verified that the catheter is not properly positioned, the method may further include adjusting the position of the catheter by aligning the proximal radiopaque marker on the ablation catheter with the respective anatomical landmark, and/or by further distancing the distal radiopaque marker from the costovertebral joint.

In any of the method aspects herein, a step of determining if the azygos vein is centered, left-biased or right biased with respect to the midline of the vertebra may comprise: imaging at least a portion of the patient's spine and vasculature, in particular the azygos vein and/or one or more intercostal veins, using an imaging device, in particular using a radiographic imaging device with a radiopaque contrast agent injected into the patient's vasculature, or imaging at least one radiopaque device, positioned in the azygos vein and/or in one or more intercostal veins, relative to a portion of the spine, using an imaging device, in particular using a radiographic imaging device, to thereby characterize the position of the patient's azygos vein relative to a midline of the spine, the radiopaque device optionally comprising a radiopaque portion of a guidewire.

In any of the method aspects herein, a step of assessing the position of the proximal radiopaque marker relative to the midline of the vertebra may comprise imaging, using an imaging device, in particular using a radiographic imaging device, at least a portion of the catheter comprising the proximal radiopaque marker.

In any of the method aspects herein, a step of assessing the position of the distal radiopaque marker relative to the costovertebral joint may comprise imaging, using an imaging device, in particular using a radiographic imaging device, at least a portion of the catheter comprising the distal radiopaque marker.

One aspect of the disclosure is a method of determining proper positioning of a catheter inserted in a vasculature of a human patient, optionally of a catheter according to any one of the claims or disclosure herein, wherein the catheter comprises an elongate shaft with a distal section carrying one or more ablation elements and a distal radiopaque marker, with the distal section of the elongate shaft positioned in a T9, T10, or T11 intercostal vein; wherein the method comprises: determining the position of the distal radiopaque marker relative to the patient's costovertebral joint, verifying if the catheter is properly positioned relative to a patient's anatomical landmark, wherein verifying comprises: considering that the catheter is properly positioned when the distal radiopaque marker is spaced from the costovertebral joint at least a prefixed threshold distance. The distal radiopaque marker may be positioned directly distal to the ablation element, or directly distal to the most distal of the ablation elements carried by the distal section of the catheter, and wherein the prefixed threshold distance is at least 3 mm, preferably at least 5 mm.

In this aspect, if it has been verified that the catheter is not properly positioned, the method may further comprise adjusting the position of the catheter by further distancing the distal radiopaque marker from the costovertebral joint.

In this aspect, a step of determining the position of the distal radiopaque marker relative to the patient's costovertebral joint may comprises imaging at least a portion of the patient's spine and vasculature, in particular the azygos vein and/or one or more intercostal veins, using an imaging device, in particular using a radiographic imaging device with a radiopaque contrast agent injected into the patient's vasculature, or imaging at least one radiopaque device, positioned in the azygos vein and/or in one or more intercostal veins, relative to a portion of the spine, using an imaging device, in particular using a radiographic imaging device, to thereby characterize the position of the patient's azygos vein relative to a midline of the spine, the radiopaque device optionally comprising a radiopaque portion of a guidewire; and imaging, using an imaging device, in particular using a radiographic imaging device, at least a portion of the catheter comprising the distance radiopaque marker.

One aspect of the disclosure is an ablation catheter for transvascular ablation of thoracic splanchnic nerves, particularly for ablating a greater splanchnic nerve or greater splanchnic nerve roots, comprising: an elongate shaft having a length such that a distal section of the elongate shaft can be positioned in a T9, T10, or T11 intercostal vein, proximal and distal electrically conductive flexible ablation elements carried by the elongate shaft distal section, a length from a distal end of the distal ablation element to a proximal end of the proximal ablation element being from 10 mm-25 mm.

In this aspect the distal section of the elongate shaft may have an outer diameter from 1.5 mm to 3 mm.

In this aspect an axial spacing may exist between the proximal and distal ablation elements that is from 0.1 mm to 5 mm, such as 0.1 mm to 3 mm, such as 0.1 mm to 2 mm, such as 5 mm to 1-mm.

In this aspect the distal and proximal ablation elements may be electrodes.

In this aspect the distal and proximal ablation elements may each have a length, wherein the lengths are the same.

In this aspect the distal and proximal ablation elements may each have a length, wherein the lengths are not the same.

In this aspect the distal and proximal ablation elements may each have a length from 5 mm to 12 mm, such as from 6 mm to 10 mm, such as from 7 mm to 9 mm, such as any integer in any of these ranges.

In this aspect the distal ablation element may have a helical configuration and wherein the proximal ablation element may a helical configuration. A helical configuration of the distal and proximal ablation elements may the same. Helical configurations of the distal and proximal ablation elements have one or more different features, such as one or more of coil direction (e.g. left-handed vs right-handed), pitch, or thickness.

In this aspect the distal and proximal ablation elements may each have curvilinear cross-sectional configurations.

In this aspect the distal and proximal ablation elements may each have rectilinear cross-sectional configurations.

In this aspect the distal and proximal ablation elements may be made from a superelastic material such as nitinol.

In this aspect distal and proximal ablation elements may be sufficiently flexible and sized to allow the distal section to be advanced from an azygos vein into one of a T9, T10, or T11 intercostal vein.

In this aspect the distal and proximal ablation elements may each be attached to the shaft at distal and proximal end regions, but not in between the distal and proximal end regions.

In this aspect the catheter may further comprise a radiopaque marker. The radiopaque marker may be disposed distal to a distal end of the distal ablation element. The radiopaque marker may be 0 mm to 5 mm distal to the distal end of the distal ablation element, optionally 0 mm to 3 mm, or 0 mm to 2 mm. The radiopaque marker may be disposed proximal to a proximal end of the proximal ablation element. The radiopaque marker may be 0 mm to 5 mm proximal to the distal proximal of the distal ablation element, optionally 0 mm to 3 mm, or 0 mm to 2 mm.

In this aspect the distal and proximal ablation elements are each not configured to deploy to a deployed configuration.

In this aspect the distal and proximal ablation elements each have an operational configuration that is the same or substantially the same as a delivery configuration.

In this aspect the distal and proximal ablation elements each have an outer diameter in an operational state that is the same or substantially the same as an outer diameter in a delivery state.

In this aspect the distal and proximal ablation elements may each have expanded configurations different than delivery configurations.

In this aspect the catheter may further comprise a temperature sensor carried by the shaft. The temperature sensor may be disposed at a distal end of the distal ablation element. The temperature sensor may be disposed at a proximal end of the proximal ablation element. The catheter may comprise a second temperature sensor, the temperature sensor disposed at a distal end of the distal ablation element, the second temperature sensor disposed at a proximal end of the proximal ablation element.

In this aspect, the catheter may further comprise one or more irrigation ports in fluid communication with an irrigation lumen that is connectable to a fluid source at a proximal region of the ablation catheter. One of the one or more irrigation ports may be axially in between the distal and proximal ablation electrodes. None of the one or more irrigation ports may be disposed radially under an ablation element structure. One or more irrigation ports may be disposed between helical windings of the distal and proximal ablation electrodes. In a side view, an irrigation port may be disposed between every adjacent pair of ablation element helical sections of the distal ablation element and the proximal ablation element.

In this aspect the distal and proximal ablation elements may be electrically configured to be independently energized in monopolar mode.

In this aspect the distal and proximal ablation elements may be electrically configured to be energized in bipolar mode.

In this aspect the distal section may be no more than 7 cm from a distal tip of the ablation catheter.

In this aspect the distal and proximal ablation elements may be sized and adapted to create a continuous ablation having a length in a range of 5 mm to 25 mm, such as 10 to 25 mm, such as 15 mm to 20 mm.

In this aspect the distal section may be adapted for flexibly traversing a bend from an azygos vein to a T9, T10 or T11 intercostal vein.

In this aspect the catheter may further comprise a guidewire lumen within the elongate shaft and having a distal port at a distal tip of the catheter.

In this aspect the distal and proximal ablation elements may each comprise one or more of an RF ablation electrode, a coiled wire electrode, a laser cut RF electrode, a RF electrode printed with conductive ink, a RF electrode on an expandable balloon (e.g., conductive ink, flexible circuits), a conductive membrane RF electrode, a RF electrodes on an expandable cage or mesh, an ultrasound ablation transducer, an electroporation electrodes, an cryoablation element, or a virtual RF electrode.

In this aspect the distal and proximal ablation elements may each be adapted and configured to deliver ablation energy circumferentially to create a circumferential lesion.

One aspect of the disclosure is an ablation catheter for transvascular ablation of thoracic splanchnic nerves, particularly for ablating a greater splanchnic nerve or greater splanchnic nerve roots, comprising: an elongate shaft having a length such that a distal section of the elongate shaft can be positioned in a T9, T10, or T11 intercostal vein, and an electrically conductive flexible ablation element carried by the elongate shaft distal section, the ablation element having a length from 10 mm-25 mm, and a radiopaque marker carried by the elongate shaft.

In this aspect the distal section of the elongate shaft may have an outer diameter from 1.5 mm to 3 mm.

In this aspect the radiopaque marker carried by the elongate shaft may be disposed from 0 mm to 5 mm from an end of the ablation element, such as from 0 to 4 mm, or from 0 to 3 mm, or 0 to 2 mm. The end may be a distal end of the ablation element. The end may be a distal end of a distal ablation electrode, and the ablation element may further comprising a proximal ablation electrode axially spaced from the distal ablation electrode.

In this aspect the end may be a proximal end of the ablation element.

In this aspect the catheter may further comprise a second radiopaque marker carried by the elongate shaft and disposed from 0 mm to 5 mm (e.g., 0 to 4 mm, 0 to 3 mm, or 0-2 mm from a second end of the ablation element).

In this aspect the ablation element may comprise distal and proximal ablation electrodes. The radiopaque marker may be distal to the distal ablation electrode, wherein catheter may include a second marker proximal to the proximal ablation electrode.

In this aspect, the radiopaque marker may be disposed from 0 mm to 3 mm from the end of the ablation element, optionally 1 mm.

In this aspect, the ablation element may comprise a distal ablation electrode axially spaced from a proximal ablation electrode. The distal and proximal ablation electrodes may each have a length, wherein the lengths are the same or wherein the lengths that are not the same. The distal and proximal ablation electrodes may each have a length from 5 mm to 12 mm. The distal and proximal ablation electrodes may be axially spaced from 0.1 mm to 5 mm apart, such as from 0.1 mm to 3 mm apart, optionally from 0.5 mm to 1 mm apart. Distal and proximal ablation elements in this aspect may be any of the distal and proximal ablation elements herein, such as coiled elements. In this aspect a cross-sectional outer profile of a distal ablation electrode may be different than a cross-sectional outer profile of a proximal ablation electrode. Distal and proximal ablation electrodes may be made from a superelastic material such as nitinol. Distal and proximal ablation electrodes may be sufficiently flexible to allow the distal region to be advanced from an azygos vein into one of a T9, T10, or T11 intercostal vein.

In this aspect, the ablation element may not be configured to deploy to a deployed configuration.

In this aspect, the ablation element may have an operational configuration that is the same or substantially the same as a delivery configuration.

In this aspect, the distal section may have a linear at-rest configuration.

In this aspect, the ablation element may have an outer diameter in an operational state that is the same or substantially the same as an outer diameter in a delivery state.

In this aspect the catheter may further comprise one or more temperature sensors carried by the shaft. A temperature sensor may be disposed at a distal end of the ablation element. A temperature sensor may be disposed at a proximal end of the ablation element. The catheter may further comprise a second temperature sensor, the temperature sensor may be disposed at or near a distal end of the ablation element, the second temperature sensor may be disposed at or near a proximal end of the ablation element.

In this aspect the catheter may comprise one or more irrigation ports in fluid communication with an irrigation lumen that is connectable to a fluid source at a proximal region of the ablation catheter, including any of the one more irrigation ports herein. One of the one or more irrigation ports may be axially in between the distal and proximal ablation electrodes. None of the one or more irrigation ports may be disposed radially under an ablation element structure. The one or more irrigation ports may be disposed between windings of the distal and proximal ablation electrodes, and wherein none of the one or more irrigation ports may be disposed radially under an ablation element structure. In a side view, an irrigation port may be disposed between every adjacent pair of ablation element helical sections.

In this aspect the ablation element may comprise first and second ablation elements, each of which may be electrically configured to be independently energized in monopolar mode.

In this aspect the ablation element may comprise first and second ablation elements that are electrically configured to be energized in bipolar mode.

In this aspect the distal section may be no more than 7 cm from a distal tip of the ablation catheter.

In this aspect the ablation element may be adapted to create an ablation having a length in a range of 10 to 25 mm, such as 15 mm to 20 mm.

In this aspect the distal section may be adapted for flexibly traversing a bend from an azygos vein to a T9, T10, or T11 intercostal vein.

In this aspect the catheter may further comprise a guidewire lumen within the elongate shaft and having a distal port at a distal tip of the catheter.

In this aspect the ablation element may comprise one or more of an RF ablation electrode, a coiled wire electrode, a laser cut RF electrode, a RF electrode printed with conductive ink, a RF electrode on an expandable balloon (e.g., conductive ink, flexible circuits), a conductive membrane RF electrode, a RF electrodes on an expandable cage or mesh, an ultrasound ablation transducer, an electroporation electrodes, an cryoablation element, or a virtual RF electrode.

In this aspect the ablation element may be adapted and configured to deliver ablation energy circumferentially to create a circumferential lesion.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 8A is a schematic illustration of an ablation catheter with two coiled RF electrodes.

FIG. 8B is a schematic illustration of an ablation catheter with two coiled RF electrodes and a distal deployable element.

FIG. 9 is a schematic illustration of an ablation catheter with two coiled RF electrodes, a distal deployable element, and a proximal deployable element.

FIG. 10 is a schematic illustration of an ablation catheter with two coiled RF electrodes, a distal deployable element, a proximal deployable element, and a middle deployable element.

FIG. 11 is a schematic illustration of an ablation catheter with an RF electrode comprising expandable wire struts.

FIG. 12 is a schematic illustration of an ablation catheter with an RF electrode comprising an expandable balloon with an RF electrode on its surface.

DETAILED DESCRIPTION

The disclosure herein is generally related to methods of treating at least one of heart failure and hypertension by increasing splanchnic capacitance. Some approaches include systems, devices, and methods for transvascular (e.g., transvenous) ablation of target tissue to increase splanchnic venous capacitance or venous compliance. The devices and methods may, in some examples, be used for ablating a splanchnic nerve to increase splanchnic capacitance. For example, the devices disclosed herein may be advanced endovascularly to a target vessel or plurality of vessels in the region of a thoracic splanchnic nerve ("TSN"), such as a preganglionic greater splanchnic nerve ("GSN"), lesser splanchnic nerve, or least splanchnic nerve or one of their roots (a TSN nerve root). The target vessel may be, for example, an intercostal vein or an azygos vein (or both) or a vein of the azygos vein system, preferably, one or more of the lowest (i.e., most caudal) three intercostal veins (which may be T9, T10, or T11).

Figure 1:
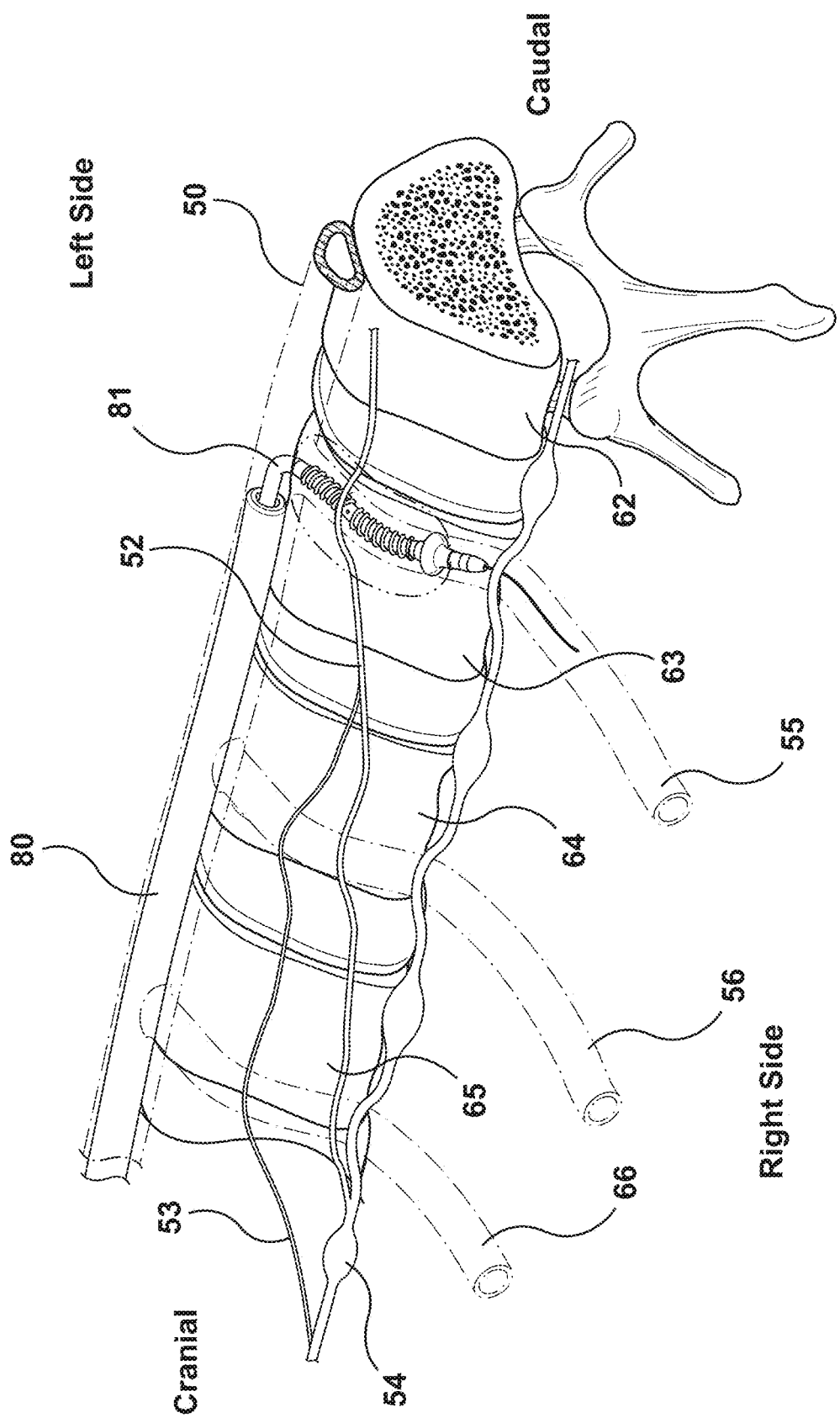
FIG. 1 is an isometric view schematic illustration of an ablation catheter positioned in an intercostal vein for ablation of a thoracic splanchnic nerve.
Figure 2:
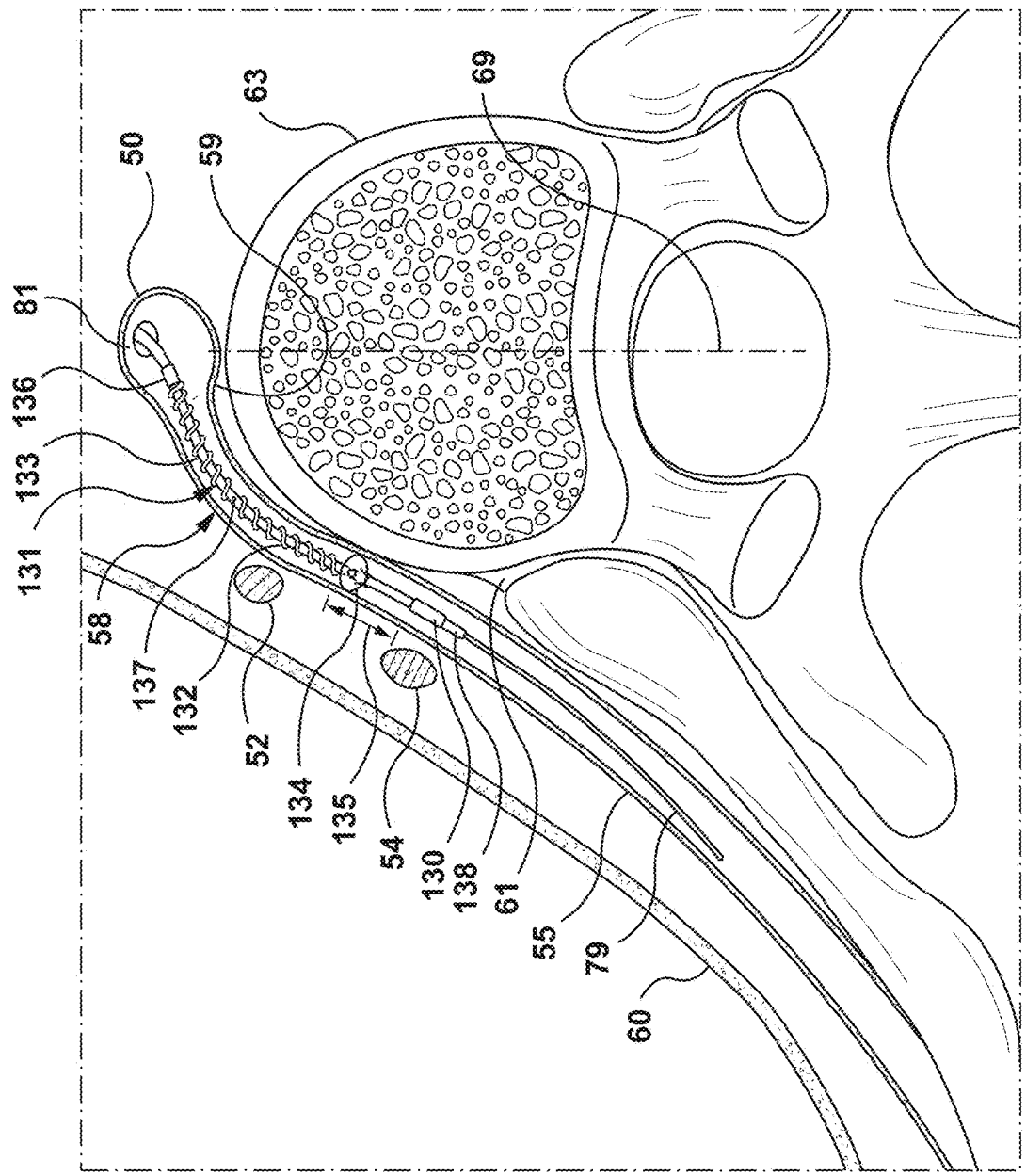
FIG. 2 is a transverse view schematic illustration of an ablation catheter positioned in an intercostal vein and a centered azygos vein.
Figure 3:
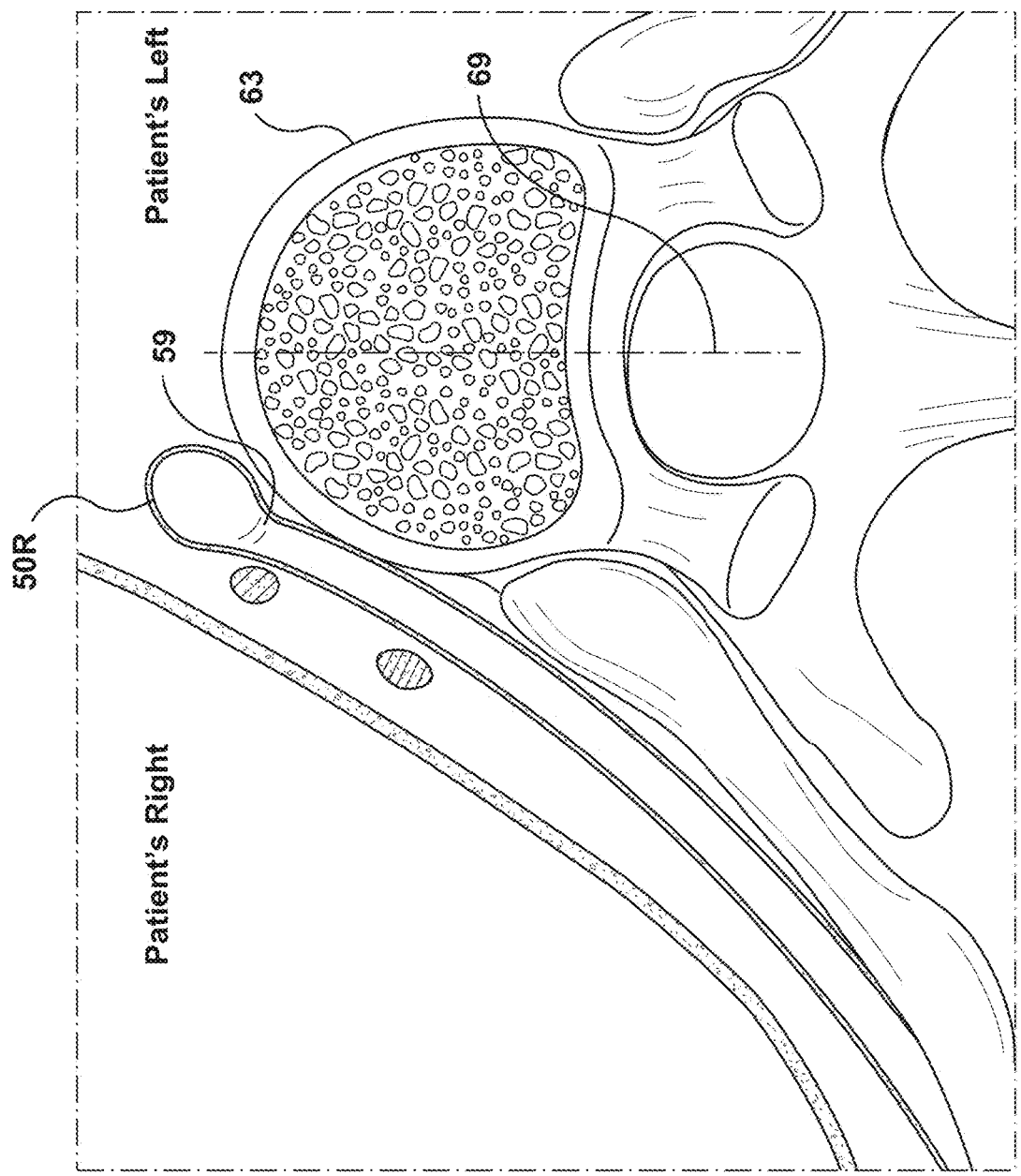
FIG. 3 is a transverse view schematic illustration of anatomy showing a right-biased azygos vein.
Figure 4:
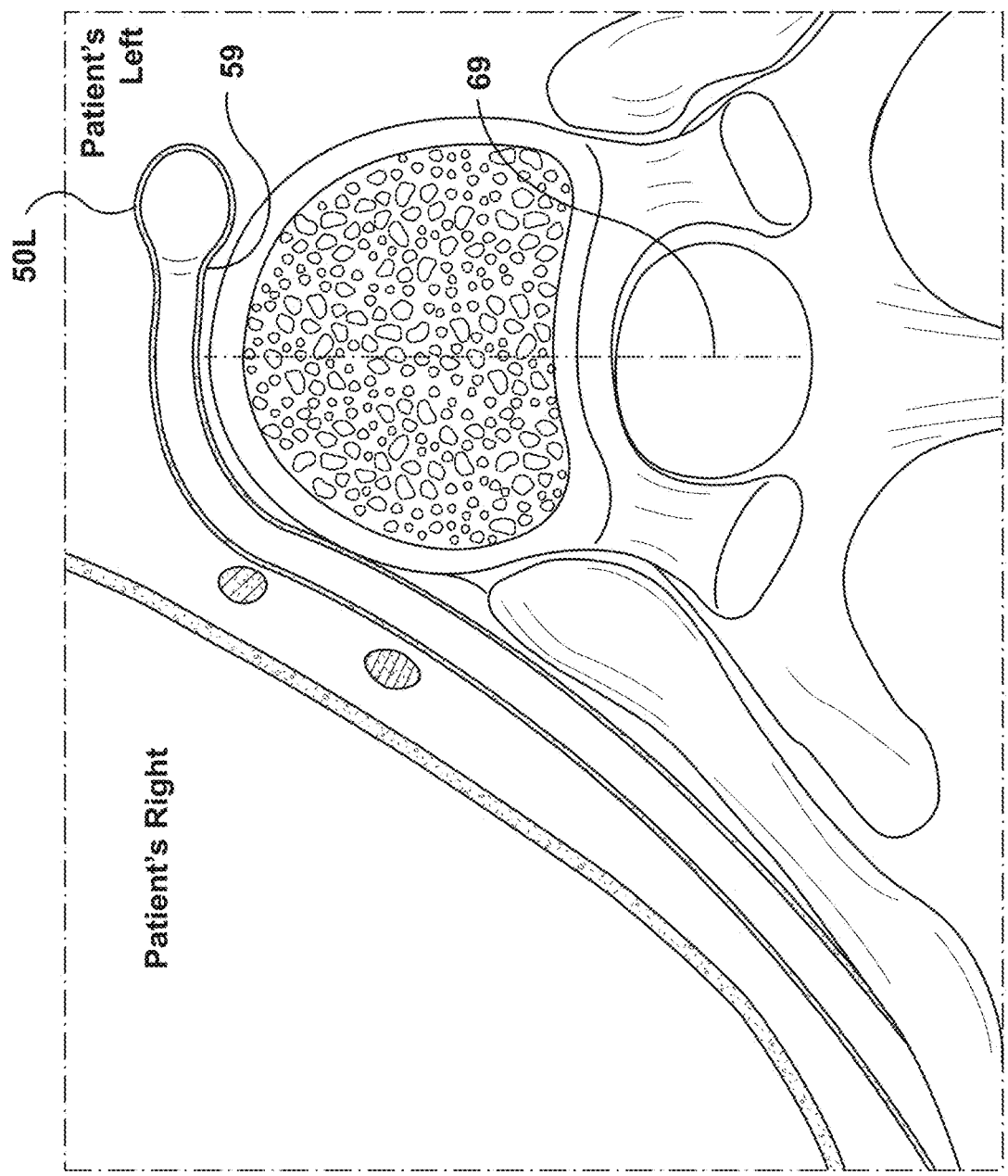
FIG. 4 is a transverse view schematic illustration of anatomy showing a left-biased azygos vein.
Figure 5:
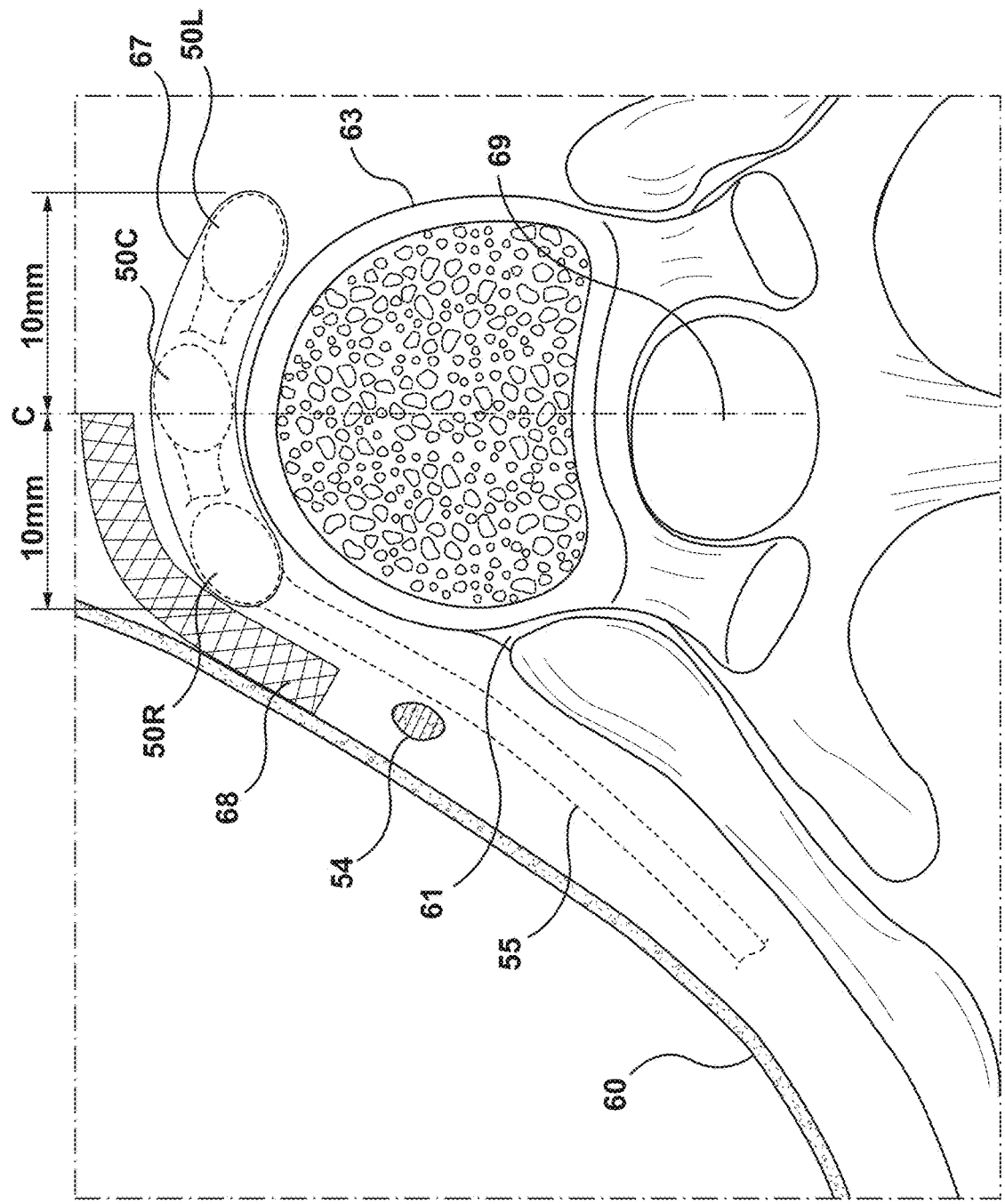
FIG. 5 is a transverse view schematic illustration of anatomy showing a range of position of azygos veins and a range of position of a right GSN.

FIG. 1 shows a patient's thoracic spine, including T12 (62), T11 (63), T10 (64), and T9 (65) vertebrae, intervertebral discs, a sympathetic trunk 54, an azygos vein 50, a right T11 intercostal vein 55, a right T10 intercostal vein 56, a right T9 intercostal vein 66, GSN roots 53, and a fully-formed GSN 52. The lesser and least splanchnic nerves and their roots are omitted for simplicity. A primary objective of the proposed procedure is to ablate the GSN or its roots as will be discussed in detail herein. It is noted that ablation of the lesser or least splanchnic nerves or their roots may also have therapeutic effects and may be a procedural objective. A delivery sheath 80 is shown positioned in the azygos vein and an ablation catheter 81 is shown delivered through the sheath and passing from the azygos vein into the T11 intercostal vein. The sympathetic trunk runs substantially parallel to the spine, consistently passing close to each costovertebral joint 61 (see FIG. 2). On the right side of the body the GSN roots branch from the sympathetic trunk, typically cranial to the T9 vertebra, and converge to form the GSN, which travels at an angle from the sympathetic trunk toward the anterior-center of the spine and is positioned anterior to the intercostal veins between the intercostal veins and parietal pleura 60 (see FIG. 2). The azygos vein 50 travels along the anterior of the spine and may be somewhat straight and parallel to the axis of the spine as shown in FIG. 1. However, the precise position of the azygos vein relative to the spine is variable from patient to patient and at different vertebral levels. At the T9, T10, and T11 vertebral levels the azygos vein 50 may be centered with respect to the midline of the vertebra 69 as shown in FIG. 2, may be a right-biased azygos vein 50R with respect to the midline of the vertebra 69 as shown in FIG. 3, or be a left-biased azygos vein 50L with respect to the midline of the vertebra 69 as shown in FIG. 4. Cadaver studies conducted by the authors indicate that the range of azygos position relative to the center of the spine at the T9, T10, and T11 levels is within 10 mm to the left or right of center for a large majority of people. FIG. 5 shows a left-biased azygos vein 50L, a right-biased azygos vein 50R, and a centered azygos vein 50C along with the range 67 of the azygos vein relative to the center of the spine 69. Furthermore, the precise position of the right GSN from patient to patient is somewhat variable including where it originates from the sympathetic trunk, the angle at which it travels, and its destination relative to the spine. Thus, the position of the GSN relative to the vertebra at T9, T10 and T11 can vary. Cadaver studies conducted by the authors indicate that the range of right side GSN position relative to the center of the vertebra at the T9, T10 and T11 levels is from 0 mm to 25 mm to the right of center 69 as shown by the range box 68 in FIG. 5.

An endovascular approach to transvascularly ablate a TSN, particularly a GSN may involve one or more of the following steps: accessing venous vasculature at the patient's jugular vein or femoral vein with an access introducer sheath (e.g. 12F); delivering a delivery sheath (e.g., 9F sheath) to an azygos vein (e.g., to one or two thoracic levels above the target intercostal vein); optionally, delivering contrast agent through the sheath to show location of veins on fluoroscopy; optionally, delivering a guidewire (e.g., 0.014" guidewire) through the delivery sheath and into a targeted T9, T10, or T11 intercostal vein; and delivering an ablation catheter through the delivery sheath to the azygos vein, optionally over the guidewire, positioning an ablation element in an intercostal vein, azygos vein or both; and aligning a radiopaque marker on the ablation catheter with an anatomical landmark (or positioning it relative thereto) to position an ablation element in a region that maximizes efficacy of ablating a target TSN/GSN while minimizing risk of injuring one or more non-target structures.

Some important anatomical structures in the vicinity of this region that should not be injured include the sympathetic trunk 54, vagus nerve, thoracic duct, and esophagus. Therefore, to ensure safety an ablation zone should be contained within a safe region that does not injure such structures. Due to the variability of position of the azygos vein and GSN relative to the T9, T10 and T11 vertebrae, the relative position of the GSN with respect to the intercostal vein or azygos vein in which an ablation element is positioned is also variable.

Bones, blood vessels if injected with radiopaque contrast medium, and medical devices if made from radiopaque material, are visible on fluoroscopy but nerves are not. An ablation device designed for transvascular (e.g. transvenous) ablation of a TSN (e.g., GSN) from an intercostal vein, azygos vein, or both along with procedural steps may be provided to ensure efficacious ablation of the TSN (e.g., GSN) while ensuring safety. The procedural steps may include fluoroscopic imaging to position the ablation element(s) of the ablation catheter with respect to boney or vascular structures.

Figure 7:
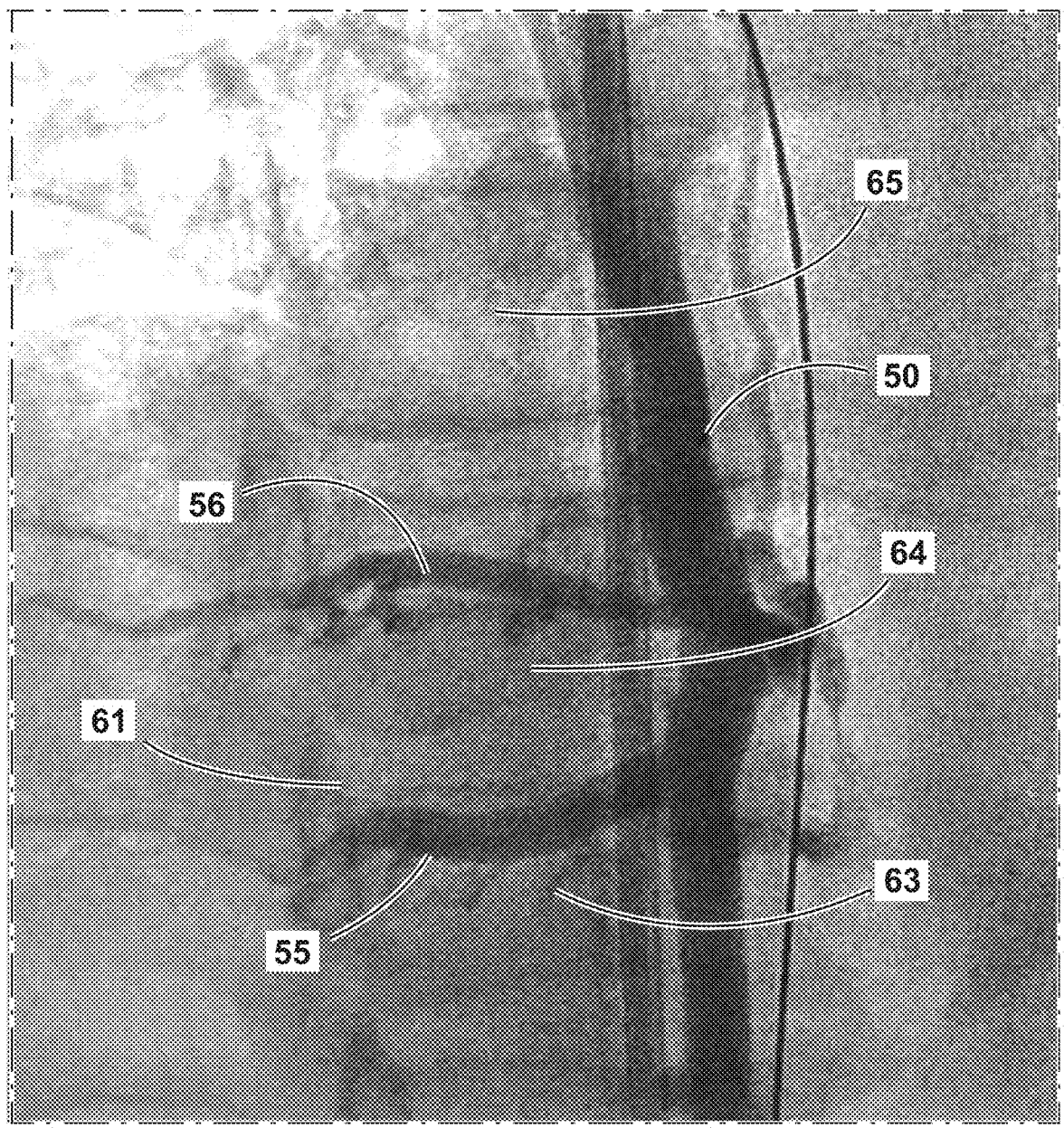
FIG. 7 is an RAO30 fluoroscopic image of a patient's T8 to T12 thoracic region.

In a first embodiment of a method of ablating a right GSN an ablation catheter having a proximal radiopaque marker 136, a distal radiopaque marker 130, an ablation element 131 or plurality of ablation elements 132, 133, and an optional gap 135 between the ablation element and the distal radiopaque marker is advanced from an azygos vein 50 into an intercostal vein 55 at one of the lower three thoracic levels (e.g. T9, T10, T11). The C-Arm is placed in Anterior-Posterior (AP) orientation. The proximal radiopaque marker 136 is aligned with the midline of the vertebra 69, which is possible if the azygos vein 50 is centered or left-biased. If the azygos vein 50 is left-biased the proximal radiopaque marker will need to be advanced into the intercostal vein to align it with the midline of the vertebra 69. If the azygos vein is right-biased the proximal radiopaque marker 136 will not be able to be placed at the midline of the vertebra 69. In this case the proximal radiopaque marker 136 may be placed at the ostium of the intercostal vein, which will be to the right of midline 69. Optionally, the position of a distal radiopaque marker 130 relative to the costovertebral joint may be assessed (e.g., with the C-Arm in a RAO orientation) to ensure the sympathetic trunk is not at risk of injury, for example with patients who are very small and have an extreme right-biased azygos vein. The C-Arm may be obliquely angled to the right (RAO orientation) to maximize the 2D projection of the section of intercostal vein between the costovertebral joint 61 and anterior midline of the vertebra 69 (FIG. 7). For example, the C-arm may be positioned with a Right Anterior Oblique (RAO) angle in a range of 20° to 70° from AP (e.g., in a range of 30° to 60°, in a range of 35° to 55°, about 30°, at an angle that maximizes projected distance between the proximal and distal RO markers). With this view the user may check to make sure the distal radiopaque marker is not too close to the costovertebral joint 61. For example, if the distal radiopaque marker is positioned directly distal to the ablation element a distance of at least 3 mm (e.g., at least 5 mm) may be chosen to ensure the sympathetic trunk is not injured. In another example, if the distal radiopaque marker is positioned distal to the ablation element with a known space between them the distal radiopaque marker may be aligned with the costovertebral joint or proximal to it to ensure safety of the sympathetic joint. If the distal radiopaque marker is too close to or beyond the costovertebral joint the catheter may be pulled back until an acceptable distance between the distal radiopaque marker and the costovertebral joint is seen, which may place the proximal radiopaque marker in the azygos vein especially if the azygos vein is right biased. If the ablation element is comprised of a plurality of ablation elements (e.g., two) an ablation may first be performed from the more proximal ablation element prior to pulling the catheter back to appropriately place the distal radiopaque marker relative to the costovertebral joint. Then a subsequent ablation may be made from the more distal ablation element.

In a second embodiment of a method of ablating a right GSN an ablation catheter having a proximal radiopaque marker 136, a distal radiopaque marker 130, an ablation element 131 or plurality of ablation elements 132, 133, and an optional gap 135 between the ablation element and the distal radiopaque marker is advanced from an azygos vein 50 into an intercostal vein 55 at one of the lower three thoracic levels (e.g. T9, T10, T11). The C-Arm is placed in Anterior-Posterior (AP) orientation. The proximal radiopaque marker 136 is aligned with the intercostal vein ostium 59. The ostium can be found for example by injecting contrast agent and viewing the vasculature on fluoroscopy or if a guidewire was previously positioned in a target intercostal vein a bend in the guidewire or ablation catheter may indicate the location of the ostium. If the azygos vein is left-biased the catheter is advanced distal to the ostium to align the proximal radiopaque marker 136 with the midline of the vertebra 69. In this placement strategy the proximal radiopaque marker 136 will be aligned with the midline of the vertebra 69 if the azygos vein is left-biased or centered, and to the right of the midline of the vertebra if the azygos vein is right-biased. Concurrently, the proximal radiopaque marker 136 will be aligned with the ostium if the azygos vein is right-biased or centered, and at the midline of the vertebra 69 if the azygos vein is left-biased. Optionally, the position of a distal radiopaque marker 130 relative to the costovertebral joint may be assessed (e.g., with the C-Arm in a RAO orientation) to ensure the sympathetic trunk is not at risk of injury, for example with patients who are very small and have an extreme right-biased azygos vein. The C-Arm may be obliquely angled to the right (RAO orientation) to maximize the 2D projection of the section of intercostal vein between the costovertebral joint 61 and anterior midline of the vertebra 69 (FIG. 7). For example, the C-arm may be positioned with a Right Anterior Oblique (RAO) angle in a range of 20° to 70° from AP (e.g., in a range of 30° to 60°, in a range of 35° to 55°, about 30°, at an angle that maximizes projected distance between the proximal and distal RO markers). With this view the user may check to make sure the distal radiopaque marker is not too close to the costovertebral joint 61. For example, if the distal radiopaque marker is positioned directly distal to the ablation element a distance of at least 3 mm (e.g., at least 5 mm) may be chosen to ensure the sympathetic trunk is not injured. In another example, if the distal radiopaque marker is positioned distal to the ablation element with a known space between them the distal radiopaque marker may be aligned with the costovertebral joint or proximal to it to ensure safety of the sympathetic joint. If the distal radiopaque marker is too close to or beyond the costovertebral joint the catheter may be pulled back until an acceptable distance between the distal radiopaque marker and the costovertebral joint is seen, which may place the proximal radiopaque marker in the azygos vein especially if the azygos vein is right biased.

Figure 6:
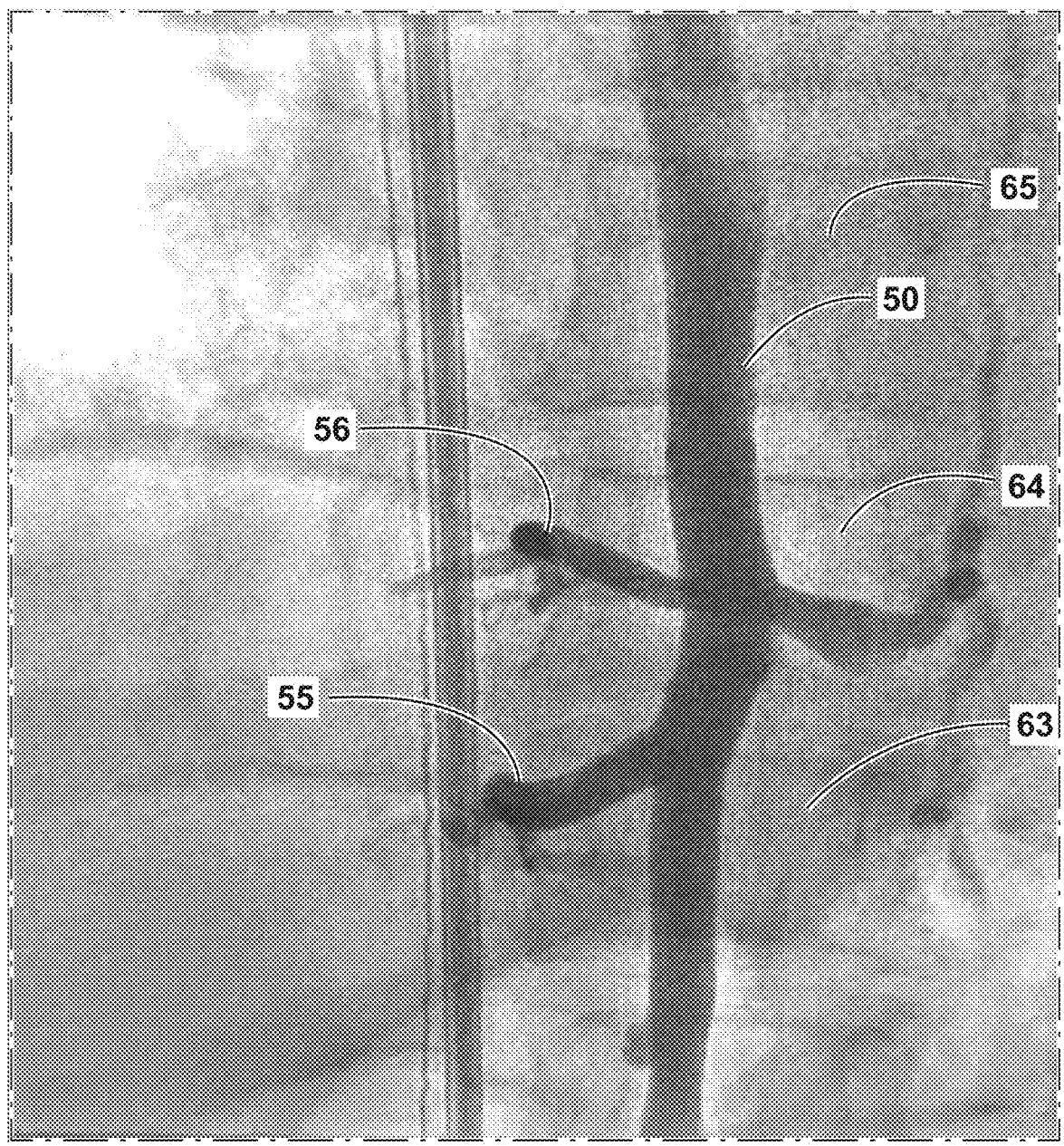
FIG. 6 is an AP fluoroscopic image of a patient's T8 to T12 thoracic region.

In a third embodiment of a method of ablating a right GSN an ablation catheter having a distal radiopaque marker 130, an ablation element 131 or plurality of ablation elements 132, 133, and a gap 135 between the ablation element and the distal radiopaque marker is advanced from an azygos vein 50 into an intercostal vein 55 at one of the lower three thoracic levels (e.g. T9, T10, T11). The C-Arm is obliquely angled to the right to maximize the 2D projection of the section of intercostal vein between the costovertebral joint 61 and anterior midline of the vertebra 69 (FIG. 2). For example, the C-arm may be positioned with a Right Anterior Oblique (RAO) angle in a range of 20° to 70° from AP (e.g., in a range of 30° to 60°, in a range of 35° to 55°, about 30°, at an angle that maximizes projected distance between the proximal and distal RO markers). A fluoroscopy image in an anterior-posterior (AP) view is shown in FIG. 6. In comparison a fluoroscopy image in a RAO 30° is shown in FIG. 7. The catheter is advanced to align the distal radiopaque marker 130 with the costovertebral joint 61. Since the sympathetic trunk 54 is next to the costovertebral joint 61 the gap between the distal radiopaque marker and the ablation element may ensure the sympathetic trunk is not injured. The gap may be for example a length in a range of 0 to 25 mm (e.g., a range of 3 to 25 mm, a range of 5 to 25 mm, a range of 5 to 20 mm). Optionally, an inflatable balloon 134 may be positioned on the catheter shaft within the gap, which may help to anchor the catheter or contain ablation energy proximal to the balloon. Optionally, the catheter shaft 138 distal to the ablation element may be narrower or more flexible than the remainder of the shaft to facilitate delivery through the narrower distal portion of the intercostal vein. Optionally, the ablation element(s) has a length capable of ablating to the anterior midline of the vertebra 69 when the distal radiopaque marker is aligned with the costovertebral joint. For example, the ablation element(s) may have a total length in a range of 5 to 25 mm (e.g., in a range of 10 to 25 mm, in a range of 15 to 20 mm). The ablation catheter may have a proximal radiopaque marker located just proximal to the ablation element(s). Optionally, prior to delivering ablation energy a user may image the proximal radiopaque marker to ensure it is at the anterior midline of the vertebra 69. If the proximal radiopaque marker is to the left of the midline 69, for example if the patient is extremely small, there may be a risk of injuring a non-target tissue such as the thoracic duct or esophagus. To mitigate this risk a catheter with a smaller sized ablation element may be used or if the ablation element is made of a plurality of ablation elements only the elements between the midline 69 and distal radiopaque marker may be activated for ablation. Conversely, if the proximal radiopaque marker is to the right of the midline 69, for example if the patient is extremely large, there may be a risk of missing the GSN. To mitigate this risk another ablation may be performed at another intercostal level or within the same intercoastal vein with the position of the ablation element retracted until the proximal radiopaque marker is aligned with the midline 69.

In a fourth embodiment of a method of ablating a right GSN an ablation catheter having an ablation element 131, which may include a plurality of ablation elements, a distal radiopaque marker located at a distal end of the ablation element(s), and a proximal radiopaque marker located at a proximal end of the ablation element(s) is advanced from an azygos vein into an intercostal vein at one of the lower three thoracic levels (e.g. T9, T10, T11). The C-Arm is obliquely angled to the right to maximize the 2D projection of the section of intercostal vein between the costovertebral joint 61 and anterior midline of the vertebra 69 (FIG. 5). For example, the C-arm may be positioned with a Right Anterior Oblique (RAO) angle in a range of 25° to 65° from AP (e.g., in a range of 30° to 60°, in a range of 35° to 55°, about 30°), The catheter is advanced to align the distal radiopaque marker with a position relative to the costovertebral joint and the opposing edge of the vertebral body in the oblique view. For example, the distal radiopaque marker may be aligned with a point that is midway between the costovertebral joint and the opposing edge of the vertebral body in the oblique view. The ablation element(s) may have a total length expected to cover the GSN position range 68 in most patients. Similar to the previously described methods, the proximal end of the ablation element(s) may be at the anterior midline of the vertebra 69 or to the left in centered or left-biased azygos situations and may be in the azygos vein in right-biased azygos situations. Ablation energy may be delivered from the ablation element(s) to ablate the range without moving the catheter. Optionally, the catheter may be moved to another intercostal level and a second ablation may be made using the same method steps.

Performing any of the exemplary embodiments of placement strategy disclosed above, when the ablation element 131 has a total length less than 30 mm (e.g., less than 25 mm, less than 20 mm, about 15 mm) it is expected that in a large majority of patients the sympathetic trunk will be spared from injury even if the azygos vein is right-biased. Additionally, when performing the methods herein, when the ablation element 131 has a total length greater than or equal to 15 mm it is expected that in a large majority of patients the GSN will be ablated. Therefore, the ablation element 131 may have a total length in a range of 15 mm to 30 mm to be effective and safe for a large majority of patients using these placement strategies. However, smaller ablation element total length may be suitable for exceptional patients. For example, the ablation element may have a total length in a range of 5 to 25 mm (e.g., in a range of 10 to 20 mm, or in a range of 10 to 15 mm).

As used herein, ablation element may refer to a single structure or a plurality of structures. For example, as used herein, ablation element may include a plurality of ablation electrodes that are axially spaced apart, and each of which may be adapted to facilitate the delivery of ablation energy.

Once acceptable ablation element placement is achieved, for example using one of the exemplary embodiments of placement strategy herein, ablation energy may be delivered from the ablation element or plurality of ablation elements without having to move the catheter. Ablation energy may be delivered from the ablation element to ablate tissue circumferentially around the intercostal vein a depth in a range of 2 mm to 10 mm (e.g., a range of 2 mm to 8 mm, a range of 3 mm to 8 mm, about 5 mm). Optionally, the procedure may be repeated at another thoracic level (e.g., a more cranial level, a more caudal level, another of T9, T10, T11 intercostal veins on the same side of the patient) especially if the azygos is right biased. Alternatively or in addition to having distal and proximal radiopaque markers at both ends of an ablation element or plurality of ablation elements, the ablation element(s) itself may be radiopaque and the same methods herein may be used to position the distal or proximal end of the ablation element(s) relative to anatomical landmarks (e.g., midline of the spine, costovertebral joint, etc.). The phrase radiopaque marker as used herein may thus describe an ablation element if the ablation element is radiopaque. In some alternative embodiments, a radiopaque markers may comprise a relatively longer radiopaque marker positioned under or next to one or more ablation elements wherein the proximal end of the long radiopaque marker is at least aligned with the proximal end of the ablation element or extending proximal of the ablation element by up to 3 mm and the distal end of the long radiopaque marker is at least aligned with the distal end of the ablation element or extending distal to the ablation element by up to 3 mm.

With any of the exemplary embodiments of placement strategy disclosed above, there may be situations when a portion of the ablation element(s) is in the azygos vein while the remainder is in the intercostal vein, in particular when the ablation catheter has an ablation element or plurality of elements having a total length in a range of 10 to 25 mm. The azygos vein is larger than the intercostal vein and has greater blood flow, which may impact the ability to create an effective ablation around the azygos vein or even in the intercostal vein and may require different energy delivery parameters than an ablation made completely in an intercostal vein. To resolve this, the ablation catheter may have a plurality of ablation elements wherein at least one is fully positioned in an intercostal vein and the remainder may be in the intercostal vein or in the azygos vein or both. Different ablation energy delivery parameters may be used for the different scenarios, for example higher power or energy may be delivered to the ablation element in the azygos vein or ablation energy may only be delivered to the element(s) that are fully or partially in the intercostal vein. The location of the plurality of ablation elements may be determined with fluoroscopic imaging or by monitoring electrical impedance between each ablation element (e.g. RF electrode) and a dispersive electrode.

Optionally, two or even three levels may be ablated, particularly if the azygos is right-biased but even if the azygos is centered or left-biased, which may further increase efficacy.

Alternative devices and methods of use may include a shorter ablation element that is used to create a relatively shorter ablation and repositioned a plurality of times to create multiple ablations within the GSN position range 68. If the azygos is centered or left-biased all ablations may be made in the intercostal vein 55 and cover the range 68. If the azygos is right-biased, ablations may be made in the intercostal vein to cover a portion of the range 68, and then ablations may be made at another intercostal level to improve the probability of ablating the GSN. Optionally, ablations may be made from the azygos vein, which may use different energy delivery parameters for example, higher energy or power.

An ablation catheter adapted to ablate a TSN (e.g., GSN) from an intercostal vein and or an azygos vein, for example using one or more of the embodiments of placement strategies disclosed herein, may have features that allow it to be delivered transvascularly to a desired location in a T9, T10, or T11 intercostal vein, be positioned relative to anatomical features to effectively ablate a target TSN while safely avoiding important non-target structures in a large majority of patients, and to deliver ablative energy capable of ablating the target TSN. The ablation catheter and system features may allow a user to ablate a TSN with relative ease and efficiency without sacrificing efficacy or safety. For example, once the ablation element(s) of the catheter are positioned (e.g., using methods disclosed herein), ablation energy may be delivered from a computerized ablation console with the press of a button or at least with minimal adjustments, repositioning, dragging, torqueing of the catheter or minimal user decisions regarding energy delivery. Even considering the variability of location of the GSN 68 and azygos vein 67 (see FIG. 5), features of ablation catheters and systems disclosed herein may allow a TSN/GSN to be ablated from one placement and energy delivery procedure or in some cases from an additional placement (e.g., in another of a T9, T10, or T11 intercostal vein) and energy delivery with a high probability of success in a large majority of patients.

An ablation catheter for transvascular ablation of a GSN may have a proximal end, a distal end, an elongate shaft therebetween, a distal section (e.g., comprising the distal-most 7 cm), and an ablation element on or at the distal section. The ablation element may be adapted to create an ablation having a length in a range of 5 mm to 25 mm, preferably 10 to 25 mm (such as 15 mm to 20 mm) and a radial depth of at least 5 mm from the vessel surface. A handle may be located on the proximal end of the catheter to contain electrical or fluid connections or facilitate handling of the catheter. The elongate shaft from a strain relief region to the distal tip may have a length of 100 cm to 140 cm (such as from 110 cm to 130 cm, such as about 120 cm) allowing the distal section to be delivered from a femoral vein access to a T11 intercostal vein in a large majority of human patients, or a length of 50 cm to 140 cm allowing the distal section to be delivered from a jugular vein access to a T11 intercostal vein in most patients. To be deliverable through a 9F delivery sheath the catheter may have a maximum outer diameter of 3 mm (e.g., 2.5 mm, 2 mm, 1.5 mm) at least in its delivery state. The catheter may optionally have a deployable structure that expands beyond this dimension once advanced from the delivery sheath and positioned in a target vessel in some embodiments. The proximal region of the elongate shaft may be adapted for pushability, kink resistance, torque transmission, and flexibility. For example, the elongate shaft from the proximal end to about 7 cm from the distal end may have a metal wire braided into an outer layer of the shaft. An example material for the elongate shaft may be extruded Pebax®. The distal section may be adapted for flexibly traversing the bend from the azygos vein to intercostal vein (e.g., having a radius of curvature>=5 mm, and angle up to 120 degrees). For example, the distal section (e.g., distal-most 7 cm) may be more flexible than a section of the catheter proximal to the distal section (such as the rest of the elongate shaft) by using a lower durometer material or more flexible braided outer layer or no braided outer layer. The maximum outer diameter of the distal section, at least in a delivery state, may be in a range of 1.5 to 3 mm. A guidewire lumen may pass through the elongate shaft with an exit port at the distal tip of the shaft. The guidewire lumen may be made from, for example, a 0.014" ID polyimide tube located in a lumen of the shaft.

The ablation catheters may have an ablation element adapted to deliver ablative energy to a target nerve up to 5 mm from the vessel surface for a total length in a range of 10 mm to 25 mm, such as 10 mm to 20 mm, such as 15 mm to 20 mm. The ablation element may be made of a plurality of ablation elements (e.g., two) positioned within a region of the shaft having a total length in a range of 10 mm to 25 mm, such as 10 to 20 mm, such as 15 mm to 20 mm even if the ablation elements are axially spaced apart. The ablation element(s) may include one or more of an RF ablation electrode, a coiled wire electrode, a laser cut RF electrode, an RF electrode printed with conductive ink, an RF electrode on an expandable balloon (e.g., made from conductive ink or flexible circuits), a conductive membrane RF electrode, an RF electrode on an expandable cage or mesh, an ultrasound ablation transducer, electroporation electrodes, a cryoablation element, or a virtual RF electrode.

The ablation element may be adapted to deliver ablation energy circumferentially, that is radially symmetric around the ablation element and around the vessel in which the ablation element is positioned. Although the GSN always passes anterior to the intercostal vein and azygos, it is safe and acceptable to ablate tissue around the intercostal or azygos veins, and ablating circumferentially may allow for a simpler and faster procedure that is also less prone to user error because aiming the energy delivery is not necessary. Features that may allow for circumferential ablation may include, without limitation, ablation electrodes that expand to contact the vessel wall evenly around the circumference of the vessel, ablation electrodes that are used with an electrically conductive fluid, electrically insulative balloons or deployable structures that contain ablative energy in a segment of a target vessel allowing it to be directed radially, ablation elements that direct ablation energy circumferentially such as cylindrical ultrasound transducers.

In some embodiments, the ablation element is an RF electrode and saline may be delivered to the vessel in fluid communication with the RF electrode. An irrigation lumen in communication with irrigation ports may located distal to the ablation element, under the ablation element (in some designs where irrigated saline can pass through the ablation element), or in a deployable structure in some embodiments). An irrigation lumen may be for example a lumen in the elongate shaft in fluid communication with a tube on the catheter's proximal end that is connectable to a fluid source and pump.

Optionally, at least one deployable occlusive structure (e.g., balloon, bellows, wire mesh, wire braid, coated wire mesh, or coated wire braid) may be positioned on the shaft distal to the ablation element. The deployable structure may function to anchor the catheter in place during energy delivery and possibly to improve safety by avoiding ablation of the sympathetic trunk by providing an electrical insulator or containing saline proximal to the deployable structure. Optionally, a deployable occlusive structure may be located just proximal to the proximal end of the ablation element(s) which may function to divert blood flowing in the azygos vein away from the ablation zone. For example, a deployable occlusive structure may be a balloon such as a urethane balloon having a length (along the axis of the shaft) of about 2.5 mm and an inflated diameter of about 2.5 mm to 7 mm (e.g., 3 mm to 6 mm, 4 mm to 5 mm). The balloon may be in fluid communication with an inflation port connecting the balloon with an inflation lumen connectable to an inflation source on the proximal end of the catheter. Optionally, the inflation lumen may be in fluid communication with an irrigation lumen connectable to an irrigation source and pump. Optionally such a catheter may have a balloon with holes that allow irrigation fluid to exit the inflated balloon and flow toward the ablation element(s).

Ablation catheters may have a proximal radiopaque marker positioned on the shaft at or proximal to the proximal end of the ablation element(s). Optionally, ablation catheters may include a distal radiopaque marker which may be positioned on the shaft at or distal to the distal end of the ablation element. Optionally, there may be a space between a distal radiopaque marker and the distal end of the ablation element, the space having a length in a range of 0.1 mm to 25 mm, such as 0.1 mm to 5 mm, such as 0.1 mm to 3 mm, such as 0.5 mm, 1 mm, or 1.5 mm. For example, as shown in FIG. 2 a distal radiopaque marker 130 may be aligned with or positioned relative to an anatomical landmark such as the costovertebral joint 61 and a space 135 (e.g., 0.1 mm to 25 mm) is between the distal radiopaque marker 130 and the distal end of the ablation element 132 ensuring the ablation element is safely distant from the sympathetic trunk 54. Optionally, a deployable structure 134 may be positioned in the space transitionable between a contracted state (OD similar to the shaft OD e.g., in a range of 1.5 mm to 3 mm) and deployed state (OD increases to a range of 3 to 7 mm). The deployable structure may be a balloon, bellows, wire mesh, wire braid, coated wire mesh, or coated wire braid.

An example of an ablation catheter that is sized and adapted for GSN ablation is shown in FIG. 2. Ablation catheter 81 has an elongated shaft sized and adapted to reach a T11 intercostal vein from an introduction site at a femoral vein or jugular vein. The distal section of catheter 81, shown positioned in an intercostal vein 55, includes a distal radiopaque marker 130 that is aligned with or positioned relative to a costovertebral joint 61, an ablation element 131 comprising or consisting of a distal conductive coiled RF electrode 132 and a proximal conductive coiled RF electrode 133, an optional inflatable balloon 134 disposed between the ablation element 131 and the distal radiopaque electrode 130. The distal radiopaque marker 130 is optionally spaced distally apart from the distal end of the ablation element 132 by a distance 135 for example in a range of 0 to 25 mm (e.g., such as a range of 0.1 mm to 20 mm, such as a range of 0.1 mm to 15 mm, a range of 0.1 mm to 3 mm, such as 0.5 mm, 1 mm, or 1.5 mm). Catheter 81 also includes a proximal radiopaque marker 136 that is located at or near a proximal edge of the ablation element 131. In some embodiments proximal radiopaque marker 136 is axially spaced between 0 mm and 25 mm from a proximal end of ablation element 31 (which may be from a proximal end of ablation element 133).

The exemplary axial distances between markers and electrodes described herein (e.g., 0 mm to 25 mm, or 0 mm to 15 mm) may be integrated into any other ablation catheter herein unless indicated herein to the contrary.

Ablation electrodes 132 and 133 (or any other ablation electrode herein) may be made from, for example, Nitinol wire coiled around the catheter shaft, which may allow the electrodes to be flexible so they can traverse a tight bend from the azygos vein to the intercostal vein and also create a long ablation (e.g. 5 to 25 mm). Nitinol is an example of a superelastic material that allows the ablation element(s) to bend when traversing anatomical bends, and then elastically return to a linear or straight configuration once the electrode is past the bend.

Any of the distal sections herein may thus be described as a distal section that has an at-rest (as manufactured) linear or straight configuration. This would be in contrast to distal sections that may revert or assume non-linear at-rest configurations (e.g., a distal section with electrodes thereon that returns to a coiled configuration).

Optionally, the ablation catheter 81 includes at least one irrigation port 137 (as shown in FIG. 2) in fluid communication with an irrigation lumen that is near the coil electrodes for delivering a fluid such as saline. Saline delivery may facilitate delivery or removal of the device, or can be used during energy delivery to improve ablation formation and prevent overheating, for example. Optionally, catheter 81 may include a guidewire lumen 82 for delivery over a guidewire 79.

FIG. 8A illustrates a portion of an exemplary ablation catheter, including at least a portion of a distal section thereof. The ablation catheter in FIG. 8A includes an ablation element that includes a distal ablation element and a proximal ablation element. The ablation element (and other ablation elements herein) includes or consists of a distal conductive coiled RF electrode 132 and a proximal conductive coiled RF electrode 133, as shown in FIG. 8A. Both distal and proximal coiled electrodes may be helical coils positioned around and at least partially on the outer surface of the shaft, optionally in a groove in the shaft. The coiled electrodes may be helical, and may have varying directions, pitches, or wire thickness, and may be made from a round wire or ribbon wire of electrically conductive material such as stainless steel or superelastic Nitinol, optionally electropolished, optionally including a radiopaque material such as platinum iridium. Alternatively, one or more coiled electrodes may be made from a laser cut tube such as a Nitinol tube forming a coiled pattern or other flexible pattern. Alternatively, the ablation element (e.g., ablation element 131) may be made from a distal and a proximal flexible electrode in the form of wire mesh or braid. Alternatively, the flexible ablation element may comprise a plurality of ring electrodes each having a length no more than 5 mm, such as 3 mm. Optionally, the flexible ablation element may have an expandable diameter transitionable from a contracted delivery state to an expanded deployed state (e.g., having an outer diameter up to about 5 mm) so it can expand to contact the vessel wall.

Electrodes herein, such as the proximal and distal electrodes herein (e.g., distal electrode 132 and proximal electrode 133) may have a length that is in a range of 4 mm to 12 mm, such as 5 mm to 11 mm, and in some embodiments they are or about 5 mm, 5.5. mm, 6 mm, 6.5 mm, 7.0 mm, 7.5 mm, 8 mm, 8.5 mm, 9 mm, 9.5. mm, 10 mm, 10.5 mm, or 11 mm. Proximal and distal electrodes may have the same or substantially the same lengths, including lengths that are in the ranges provided herein (e.g., 5 mm to 11 mm). In some embodiments electrodes may have different lengths. For example, in some examples distal electrode 132 may be longer than proximal electrode 133, but the electrodes individually may have any of the lengths herein. In some examples distal electrode 132 may be shorter than proximal electrode 133, but the electrodes individually may have any of the lengths herein.

For catheters that have a plurality of electrodes, each electrode may be connected to an independent conductor passing through the elongate shaft to the proximal region of the catheter where it is connectable to an extension cable or ablation energy source. This can allow each electrode to be independently energized in monopolar mode or bipolar mode.

For some catheters with distal and proximal electrodes, the catheters may include a gap between a distal end of the proximal electrode and a proximal end of the distal electrode. In some embodiments the gap may be in a range of 0 to 5 mm, such as 0 mm 4 mm, such as 0.1 mm to 1.25 mm, such as 0.25 mm, 0.5 mm, 0.75 mm, 1 mm, or 1.25 mm. Preferably the proximal and distal electrodes are not in electrical communication with one another. Alternatively, the proximal and distal electrodes may at least partially overlap one another along their lengths as long as they are not in electrical communication with one another.

A gap between proximal and distal electrodes may be such that it is not so large that it prevents a continuous ablation lesion to be formed. Gaps described herein (e.g., 0 mm to 5 mm, such as 0.1 mm to 1.25 mm, such as 0.25 mm, 0.5 mm, 0.75 mm, 1 mm, or 1.25 mm) can provide the exemplary benefit of providing for continuous lesion formation.

Ablation catheters herein may include one or more temperature sensors. FIG. 8A illustrates an exemplary ablation catheter that comprises at least one temperature sensor. The ablation catheter shown includes, for example, a proximal temperature sensor 139 that may be positioned in contact with proximal electrode 133, and optionally on the proximal end of proximal electrode 133. The ablation catheter shown also includes a distal temperature sensor 140 that may be positioned in contact with distal electrode 132, and optionally on the distal end of the distal electrode. Any of the ablation catheters herein may optionally include another temperature sensor that may be positioned between proximal and distal electrodes, or between a plurality of electrodes. For catheters that include one or more temperature sensors, the temperature sensor(s) may be thermocouples (e.g., T-type) or thermistors. Optionally, at least one temperature sensor may radially extend or be radially extendable from the catheter shaft to contact tissue up to 3 mm away from the catheter surface. The temperature sensor(s) may be connectable at the proximal region of the catheter to a computerized energy delivery console where signals from the sensors may be input and used in an energy delivery control algorithm.

Any of the ablation catheters herein may include one or more irrigation ports (which may be referred to herein as holes or apertures) in fluid communication with an irrigation lumen that is connectable to a fluid source at the proximal region of the catheter for delivering a fluid such as saline (e.g., normal or hypertonic saline) to the vessel. The ports may be formed in one or more layers of the elongate shaft to create the fluid communication between the port and the irrigation lumen. The fluid may function to cool or remove heat from the electrode(s) and/or vessel wall, to flush blood from the vessel to reduce risk of clot formation or improve ablation consistency, to conduct electrical energy from the ablation electrodes, to control pressure in the vessel, to facilitate delivery of the distal section of the ablation catheter to a target vessel (e.g., intercostal vein), or to facilitate removal of the distal section of the ablation catheter from the target vessel. Optionally, one or more irrigation ports may be distal to the ablation element(s), or distal to each of the plurality of flexible ablation elements. In some embodiments, any of the irrigation port(s) may be positioned radially under the flexible ablation element(s). In some embodiments, one or all irrigation ports may be disposed between windings of coiled ablation element, such that the port is not radially under the winding of the ablation element. Optionally, an irrigation port may be positioned in an axial gap or space between adjacent ablation electrodes. Optionally, one or more irrigation ports may be in a cavity of a deployable occlusive structure (e.g. balloon) and may function to inflate the balloon, wherein the balloon may have a perforation on its proximal side that allows the fluid to escape the balloon into the target region of the vessel.

FIGS. 8A-10 illustrate distal sections of ablation catheters that include irrigation ports between windings of coiled ablation elements (although only one port 137 is labeled, the others can be seen in the figures). In the side views shown in FIGS. 8A-10, the exemplary ports are linearly aligned, parallel to a long axis of the distal section. Additionally shown in the side views of FIGS. 8A-10, there is an irrigation port between every adjacent pair of winding material (even though coiled elements 132 and 133 are each formed by a continuous winding along their lengths). The central port 137 between the ablation elements may or may not be included. In any of the embodiments, every port in the distal section may be between a winding (in the side view). Alternatively stated, in any of the embodiments, none of the ports may be radially under a winding structure.

Optionally, the ablation catheter may have a deployable element transitionable from a contracted delivery state (e.g., having an OD in a range of 1.5 mm to 3 mm) to an expanded deployed state (e.g., having an OD in a range of 2.5 mm to 6 mm) that functions to one or more of anchor the distal section of the catheter in the target region of the vessel, to occlude blood flow, to contain delivered fluid such as saline, to maintain vessel patency, or to act as an electrical insulator. For example, as shown in FIG. 8B, any catheter herein may also include a distal deployable element 134 coupled with optimized irrigation flow that may create a virtual electrode that provides an effective ablation without the need for wall contact. Distal deployable element 134 may be a balloon (e.g., compliant balloon) as shown in FIG. 8B, or alternatively a bellows or coated stent or mesh. Distal deployable element 134 is distal to the ablation element, which may include proximal and distal electrodes as shown in FIG. 8B.

Optionally, any of the ablation catheters herein may have a proximal deployable element. FIG. 9 illustrates an exemplary ablation catheter that includes proximal deployable element 141 that can be contracted to have an OD in a range of 1.5 to 3 mm in a delivery state, and be deployed to have an OD in a range of 4 to 10 mm in a deployed state as shown in FIG. 9. The proximal deployable element 141 may function to one or more of anchor the distal section of the catheter in the target region of the vessel, to occlude blood flow, to contain delivered fluid such as saline, to act as an electrical insulator, to maintain vessel patency, to act as a depth stopper (e.g., having a deployed OD larger than the targeted intercostal vein) to prevent the distal section from being advanced too far into the intercostal vein, or to direct blood flow in the azygos vein away from the ostium to facilitate ablation near the ostium. A proximal deployable element and a distal deployable element coupled with optimized irrigation flow may create a virtual electrode that provides an effective ablation without the need for wall contact. A proximal deployable element may be a balloon (e.g., compliant balloon) as shown in FIG. 9, or alternatively a bellows or coated stent or mesh. Any of the catheters herein may include a proximal deployable element and a distal deployable element.

Optionally, any of the ablation catheters herein may include a middle or central deployable element. FIG. 10 illustrates an exemplary ablation catheter that includes a middle deployable element 142 that can be contracted to have an OD in a range of 1.5 to 3 mm in a delivery state, and be deployed to an expanded state (e.g., having an OD in a range of 2.5 mm to 6 mm) as shown in FIG. 10. The middle deployable element may function to one or more of anchor the distal section in the target region of the vessel, to occlude blood flow, to contain delivered fluid such as saline, to maintain vessel patency, or to act as an electrical insulator. A middle deployable element may be used to isolate the vessel between a distal deployable element and the middle deployable element and around the distal ablation element to create a virtual electrode that provides an effective ablation without the need for wall contact. Likewise, the section of vessel between the middle deployable element and a proximal deployable element may be isolated. The middle deployable element may be a balloon (e.g., compliant balloon) as shown in FIG. 10, or alternatively a bellows or coated stent or mesh. In an embodiment wherein the ablation energy is electroporation, the middle deployable element may function as an electrical insulator to direct electrical current out of the vessel in through tissue around the vessel to more effectively ablate the target nerve. In alternative embodiments, an ablation catheter may have a middle deployable element and only a distal deployable element (i.e., no proximal deployable element) or only a proximal deployable element (i.e., no distal deployable element).

The disclosure above described exemplary methods of positioning an ablation catheter within an intercostal vein to ablate a GSN while minimizing or avoiding damage to non-target structures. The ablation catheters above, including those shown in FIGS. 8A, 8B, 9, and 10, included one or more radiopaque markers (e.g., distal marker 130 and proximal marker 136) that can be used as part of those methods of positioning. While the ablation catheters in FIGS. 8A, 8B, 9 and 10 are examples of ablation catheters that can be used when performing the methods herein, it is understood that the methods can be performed with a variety of ablation catheters. It is thus understood that the methods herein are not limited by the particular ablation catheters herein. It is also understood that the ablation catheters herein need not be used with the positioning methods herein.

Alternative embodiments of TSN/GSN ablation catheters may have one or more the features that are described herein, such as proximal and distal radiopaque markers spaced as described, irrigation lumens(s), temperature sensor(s), guide wire lumens, flexible shaft section, and may also include alternative ablation elements. For example, ablation elements may be RF electrodes having different configurations or ablation elements that deliver a different type of ablation energy such as ultrasound, electroporation, cryoablation, laser, chemical or other ablation modality. Ablation catheter features that are described with respect to one embodiment or example herein may be incorporated into other suitable embodiments unless the disclosure indicates otherwise. Features with the same or similar reference numbers are understood to be optionally included and can be the same component.

For example. FIG. 11 illustrates a distal section of an ablation catheter. The ablation catheter includes an ablation element that may be an RF electrode that includes a plurality of wire struts 143 running the length of the ablation element and arranged around the circumference of the shaft. The wire struts are electrically conductive. for example made from stainless steel, Nitinol or the like, and transitionable from a contracted delivery state (e.g., having an OD in a range of 1.5 to 3 mm) to an expanded deployed state (e.g., having an OD in a range of 2.5 mm to 6 mm) to contact the vessel wall, in particular an intercostal vein. The wire struts may be deployed by applying tension to a pull wire that moves a collar holding or otherwise secured to one end of the wire struts, shortening the distance between the two ends, which causes the wire struts to bend outward. The struts may be heat set in a biased configuration, such as those shown in FIG. 11. Optionally, an RF electrode may have multiple (e.g., two) RF electrodes made of wire struts, wherein the multiple electrodes are positioned next to one another similar to the coiled electrodes shown in FIGS. 8 to 10. Optionally, the wire struts may be made from a laser cut tube. Optionally the distal end, proximal end or both ends of the expandable wire electrode may have a membrane that functions to occlude the vessel when expanded and function similar to the deployable structures (e.g., balloons) shown in FIGS. 8A to 10.

Figure 13A:
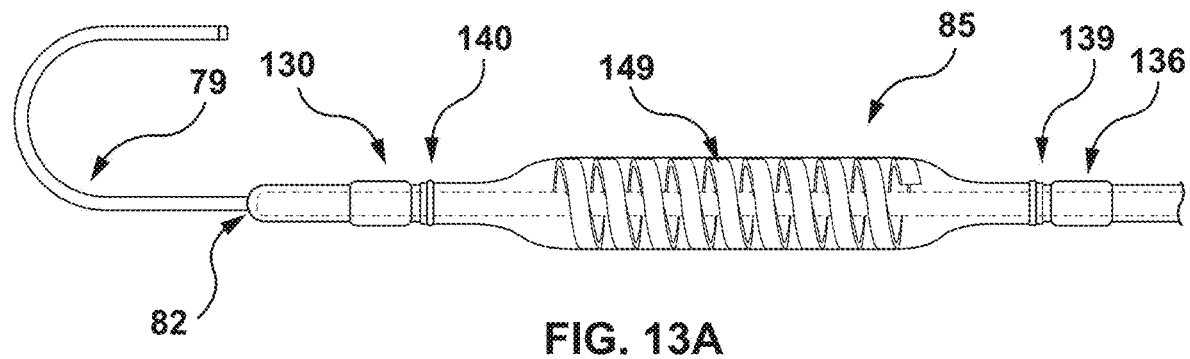
FIGS. 13A and 13B are schematic illustrations of an ablation catheter with an RF electrode comprising an expandable balloon with an RF electrode made from conductive ink on its surface.
Figure 13B:
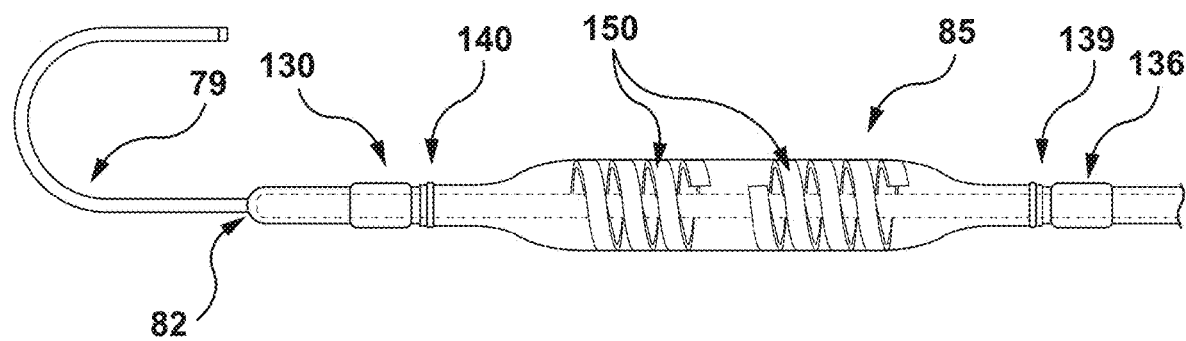
Figure 14:
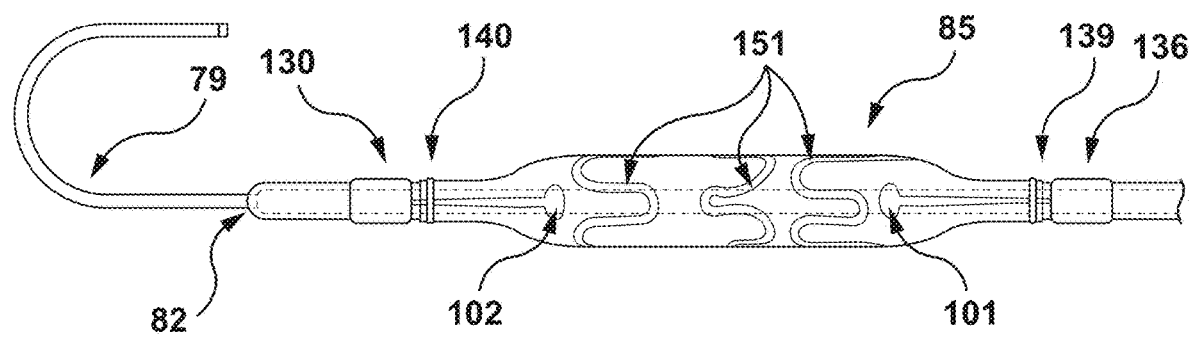
FIG. 14 is a schematic illustration of an ablation catheter with an RF electrode comprising an expandable balloon with an RF electrode on its surface in a zig-zag pattern.

FIG. 12 illustrates an exemplary ablation catheter with ablation element(s) carried by a expandable balloon. FIG. 12 illustrates a distal section of an ablation catheter with an RF ablation element, wherein the ablation element includes one or more electrically conductive element(s) positioned on expandable balloon 144. The conductive elements may be a film or conductive ink or flexible circuits. Sensors (e.g., temperature sensors) may be positioned on the balloon as well. Optionally the balloon may be inflated by delivering fluid such as saline or air into the balloon. Optionally, the conductive element(s) or the balloon may have perforations allowing fluid to pass through to cool the electrode or conduct energy. The pattern of the conductive element(s)

may be cylindrical 148 (FIG. 12), helical 149 (FIG. 13A), a plurality of electrodes each having a helical configuration 150 (FIG. 13B), electrodes with a wavy (e.g., sine wave) or zig-zag pattern 151 (FIG. 14), or other pattern adapted to circumferentially ablate around a vessel. The examples shown in FIGS. 12 to 14 include optional distal and proximal radiopaque markers that can be used with any of the methods of positioning described above.

Figure 15:
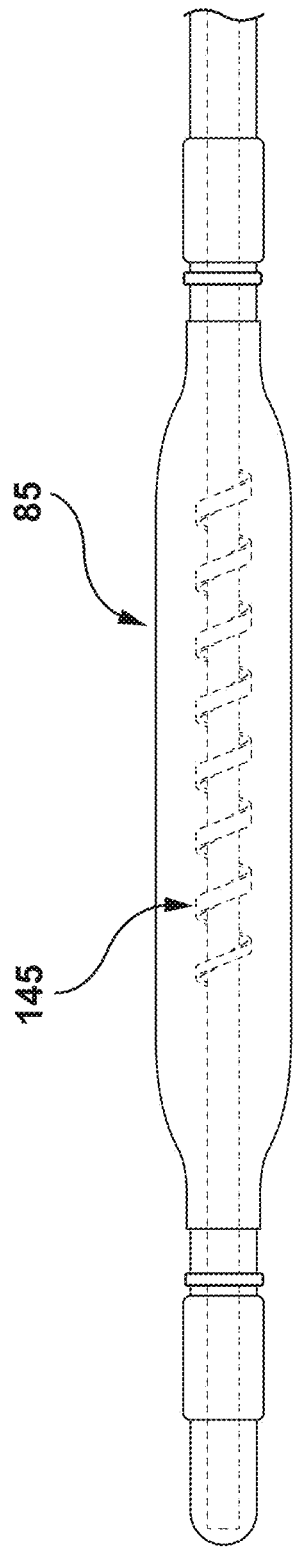
FIG. 15 is a schematic illustration of an ablation catheter with an RF electrode in a cavity defined by a membrane.

FIG. 15 illustrates an additional exemplary distal section of an ablation catheter that includes an electrically conductive element within a membrane. The catheter in FIG. 15 includes an RF ablation element that is an electrically conductive wire 145 (e.g., wire coil) on or around the catheter shaft within a cavity defined by a membrane 185. The membrane may be an ionomer, a conductive membrane, or a weeping membrane. The optional distal and proximal markers are shown distal and proximal to the balloon, respectively.

Figure 16:
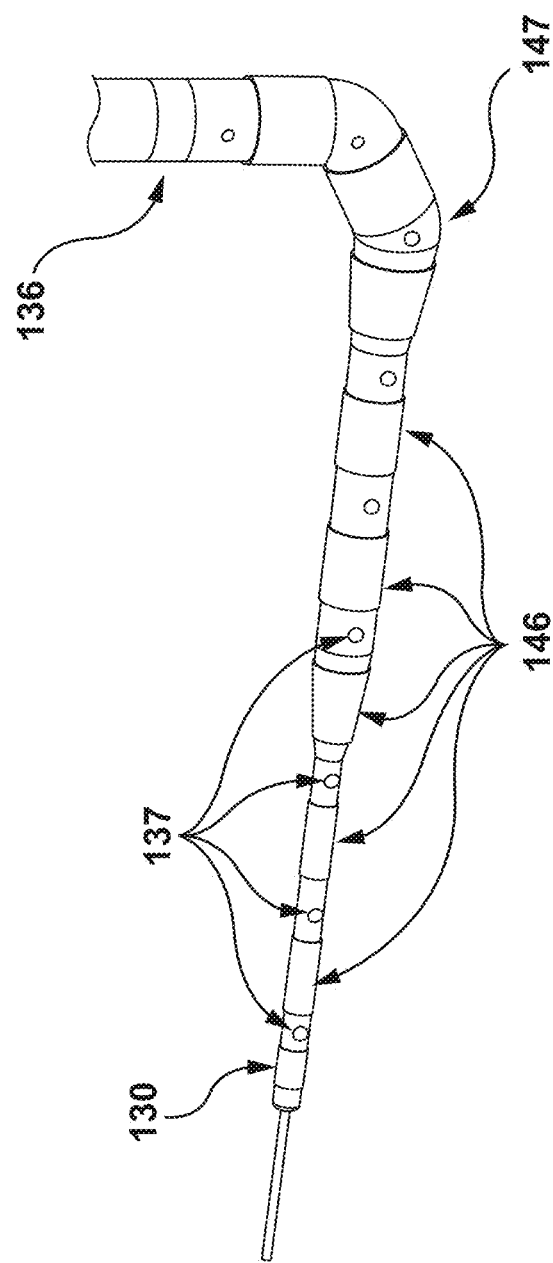
FIG. 16 is a schematic illustration of an ablation catheter with a plurality of RF electrode sections on a tapered shaft

FIG. 16 illustrates an example of a distal section of an ablation catheter, which can may be used with the methods of positioning herein. Another embodiment of an RF ablation element is shown in FIG. 16 wherein the ablation elements are a plurality of shorter RF electrodes 146 on a tapered shaft 147. This embodiment is different in that the total length of the shaft carrying ablation elements may be longer than previously described as 5 mm to 25 mm (preferably 10 mm to 15 mm). Instead, the catheter includes multiple sections (e.g., two or three) that each have a length in this range, but are selectively chosen to deliver ablation energy depending on how they fit in the intercostal vein. The tapered shaft may function to fit a range of intercostal veins (e.g., in a range of 2.5 mm to 5 mm). The distal end is narrower than the proximal end and the electrodes may be independently and selectively energized. If the distal section of the catheter is delivered to a relatively narrow intercostal vein, for example having an inner diameter of about 2.5 mm, the distal narrow portion may be advanced into the vein and selected for energy delivery, while the proximal larger portion may remain in the azygos vein and not used to delivery ablation energy. If the intercostal vein is larger, for example 5 mm inner diameter, the distal section may be advanced further into the intercostal vein until the larger electrodes are wedged into the vessel contacting the wall. The larger proximal electrodes may be selected for energy delivery while the distal electrodes are inactive to avoid injury to the sympathetic trunk. Optionally and intermediate section of electrodes may be sized to fit an intercostal vein having an inner diameter of about 3.5 mm. The plurality of electrodes may be coiled wire, laser cut tube, or solid electrodes. The electrodes may be radiopaque or have radiopaque markers associated with them so the user can image where the electrodes are positioned in the intercostal vein and choose which section of electrodes to activate.

Figures 17A, 17B:
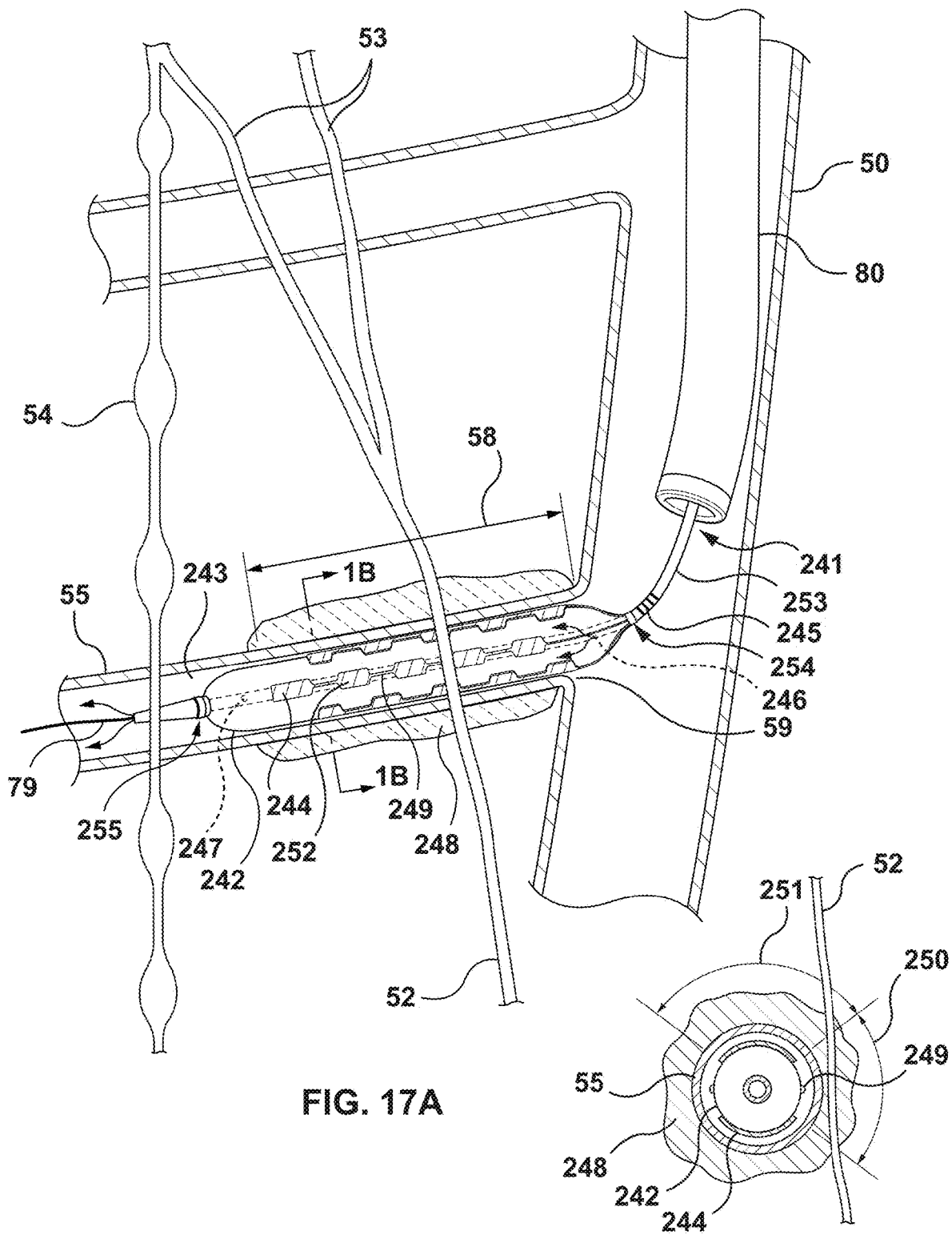
FIGS. 17A and 17B are schematic illustrations of an ablation catheter with RF electrode pads on an expandable balloon.

Another embodiment of a transvascular ablation catheter 241 for ablating a TSN or GSN from within an intercostal nerve is shown in FIG. 17A. The catheter 241 may extend along a longitudinal axis. An expandable member, for example in the form of a balloon 242 having an unexpanded state and an expanded state, may be coupled to a distal section 243 of the catheter. The expandable member (e.g., balloon) may have a circumferential treatment zone 248 (e.g., having a length in a range of 5 to 25 mm, in a range of 10 to 15 mm) extending along the longitudinal axis in the expanded state and surrounding the vessel 55. The catheter includes an electrode assembly 252, which comprises a plurality of electrode pads 244, may be mounted or otherwise secured to the balloon 242. Each electrode pad assembly may include a substrate supporting first and second electrode pads with each electrode pad having a pair of elongate bipolar electrodes and connected with an electrical trace 249. The electrode pads of each electrode pad assembly may be longitudinally and circumferentially offset from one another. The method may also include expanding the balloon in the intercostal vein so as to electrically couple the electrodes with a wall of the intercostal vein and driving bipolar energy between the electrodes of each bipolar pair so as to therapeutically alter the TSN or GSN within 5 mm of the intercostal vein such that the blood volume of the patient is redistributed for treatment of diseases such as pulmonary hypertension, or heart failure (e.g. HFpEF).

Each electrode pad may include a temperature sensor disposed between the electrodes of the pair. The expanding of the balloon may couple the temperature sensors with the wall of the intercostal vein. In some embodiments, the method may further include directing the energy to the bipolar pairs in response to a temperature signal from the temperature sensor so as to heat the wall approximately evenly.

To create an ablation having a depth of 5 mm to target a GSN from an intercostal vein the electrode pads may be cooled to allow greater power to be delivered without desiccating tissue of the vein wall, which impedes ablation depth. The electrodes may be cooled for example, by circulating coolant in the balloon 242. In one embodiment coolant may be injected into the balloon 242 from a coolant injection port 246 at one end of the balloon chamber and the coolant may exit the chamber through an exit port 247 at the opposing end of the chamber and allowed to return through the catheter through an exit lumen.

In another embodiment coolant may be deposited into the blood stream instead of returning through a lumen in the catheter. This embodiment may allow a thinner, more flexible catheter shaft or a larger coolant delivery lumen to increase flow rate of the coolant. A coolant exit port may be smaller than the coolant injection port to allow pressure to increase in the balloon to inflate it. The coolant exit port may be in communication with a lumen that does not pass through the full catheter shaft to the proximal end but instead passes to the distal end of the catheter to deposit the coolant (e.g., normal saline) into the intercostal vein. Optionally the coolant exit lumen may be the same lumen as a guidewire delivery lumen.

Electrode pads may be positioned around the balloon to make a circumferential ablation pattern that is as long as the target ablation zone 58 (e.g., up to 20 mm, about 15 mm, between 12 and 18 mm). For example, as shown in FIG. 17B, a balloon with electrode pads mounted to an elongate shaft 253 may have an undeployed state having a diameter of about 1 mm to 2.5 mm and a circumference of about 3.14 mm to 7.85 mm and be expandable to a deployed state having a diameter in a range of about 3 mm to 5 mm and a circumference in a range of about 9.4 mm to 15.7 mm. Electrode pads 244 may be separated or spaced by a distance 250 of less than 5 mm (e.g., less than 2.5 mm) and width or arc length 251 in a range of 3 mm to 3.5 mm. Electrode pads 244 may have a length of about 3 to 5 mm each. As shown in FIG. 17A, an electrode pad assembly 252 may comprise multiple electrode pads 244 arranged on four separate rows connected together by electrical traces 249, the rows evenly spaced around the circumference of the balloon 242 (e.g., four rows at each 90 degree quadrant). Longitudinally, the pads 244 on one row may be offset from pads of adjacent rows. When the balloon is in its unexpanded state the space between the electrode pads is decreased (e.g., to about 0 to 1 mm) and the adjacent rows interlock with one another. In its expanded state the space 250 between the pads expands due to the expandable balloon 242 to about 2 mm to 5 mm. The balloon 242 may be a compliant material such as latex or a non-compliant material that flexibly folds to contract.

Alternatively, electrode pads may be positioned only on one side (e.g., 50%, 40%, 30%, 25% of the balloon's circumference) to generate a directional ablation pattern that is all toward the same side and of a length of the target ablation zone 58. For a directional ablation catheter, a radiopaque marker may be positioned on the distal section of the catheter to indicate radial direction. For example, a radiopaque marker may be asymmetric and positioned on the same side or opposing side as the directional electrode pads to indicate and in use a physician may torque the catheter to aim the radiopaque marker and thus the electrode pads away from the vertebra, which is always toward the GSN. FIG. 17A shows several small electrode pads. Alternatively, the device may have larger and fewer electrode pads, for example two or three directional electrode pads (e.g., 3 to 5 mm long) on the same side of the balloon that span the target ablation zone 58. A gap (e.g., 1 to 3 mm) between electrode pads may facilitate bending of the device to traverse from the azygos vein to the intercostal vein. The ablation catheter in FIGS. 17A and 17B can include proximal and/or distal radiopaque markers, and may be used with methods of positioning described herein.

Just proximal to the balloon the catheter shaft may comprise a flexible neck 245 that allows the ablation balloon to sit in the intercostal vein's natural orientation. Given the small bend radius at this location a stiff shaft could apply force to the ablation balloon causing it to distort the intercostal vein and reduce predictability of ablation zone. A flexible neck may be made of a softer durometer polymer (e.g., Pebax®) and may have a wire coil embedded in the material, which may allow flexible bending while providing pushability. This type of flexible neck may be incorporated into other ablation catheters herein.

The electrode(s) that are most proximal may be placed just in the intercostal vein near the ostium. Blood flow through the azygos vein may metabolically cool tissue near it impeding ablation creation. A larger amount of ablation power (e.g., RF) or longer duration may be delivered to this proximal electrode(s) than the rest of the electrode(s) to compensate for the blood flow cooling.

The catheter 241 may have a distal radiopaque marker 255 positioned distal to the ablation elements, for example distal to the balloon 242, and/or a proximal radiopaque marker 254 positioned proximal to the ablation elements 244, for example proximal to the balloon 242. The distal and proximal radiopaque markers 255, 254 may be separated along the longitudinal axis of the shaft by a distance in a range of 5 mm to 25 mm (e.g., 10 mm to 15 mm). Any other features or description of radiopaque markers herein may apply to markers 255 and/or 254.

Figure 18:
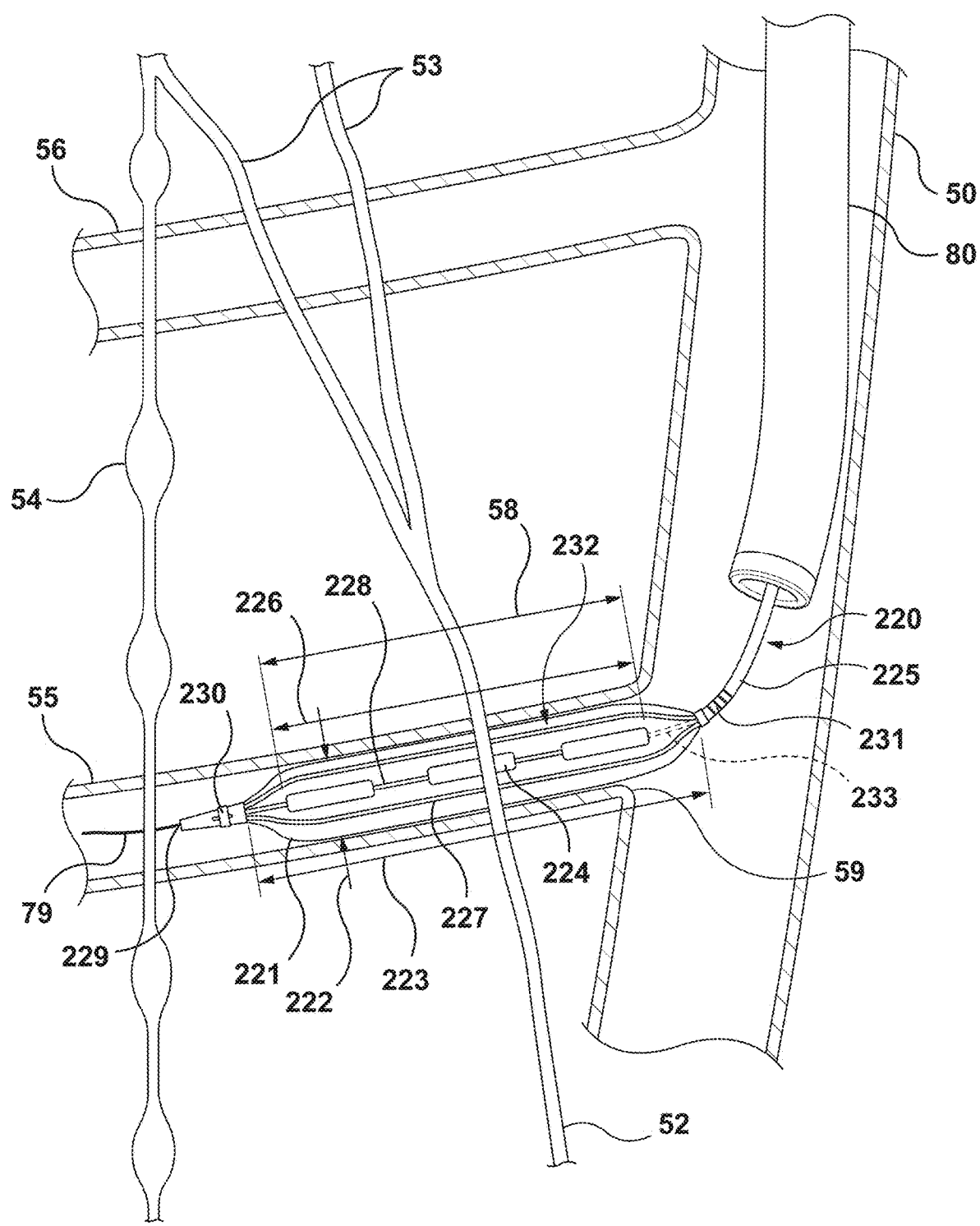
FIG. 18 is a schematic illustration of an ablation catheter with ultrasound transducers.

FIG. 18A illustrates an exemplary ultrasound ablation catheter. Catheter 220 includes an elongate shaft 225 with a proximal region and a distal section and an ablation assembly 232 mounted to or at the distal section. The ultrasound ablation catheter 220 has an inflatable balloon 221 which may have a geometry suitable for expansion in an intercostal vein (e.g., outer diameter 222 in a range of 2.5 to 5 mm in its inflated state) and a length 223 in a range of 8 to 30 mm. Within the balloon 221, multiple ultrasound transducers 224 are positioned on a shaft 233 centered in the balloon 221. The transducers 224 may be placed serially spanning a length 226 that is in a range of 5 to 25 mm to generate an ablation of a similar length capable of creating an ablation the length of the target ablation zone 58. Due to the small diameter of the intercostal vein the reduced balloon size may risk contacting the transducer or getting over heated by the transducer, which may rupture the balloon or reduce efficacy of the ablation. To remedy this risk struts or protrusions 227 may be positioned between the transducer and balloon. The struts 227 may be for example polymer strands elastically pre-shaped to radially expand away from the transducers 224. To make a longer ablation to span the targeted ablation zone, multiple transducers may be incorporated (e.g., three 4 mm long transducers) and spaced apart with flexible gaps 228 between them to facilitate traversing the small bend radius from the azygos vein to intercostal vein. For example, shaft 225 may be a braid reinforced polyimide tube with an optional guidewire lumen 229 for delivery over a guidewire 79 and carry electrical conductors that energize the transducers 224. The ultrasound transducers 224 may be cylindrical for producing circumferential ablation around the target vein. Alternatively, the ultrasound transducers may be flat or hemicylindrical to produce an ablation that is a partial segment of the circumference of the vein and a radially identifiable radiopaque marker 230 may be positioned on the distal section allowing a user to orient the direction of ablation toward the patient's anterior where the GSN passes over the vein 55. Optionally, the ultrasound transducer may be configured to image as well as ablate and the imaging function may be used to assess nearby structures such as the lung, vertebra, ribs. Imaging ultrasound may be used to confirm the transducer is aiming toward the lung, which is the direction of the target GSN. Optionally, the shaft may have a flexible neck 231 within 10 mm proximal of the balloon 221 to allow the distal section to sit well in the intercostal vein.

In an alternative embodiment of an ultrasound ablation catheter, the catheter can be composed of an active ultrasound transducer and an inflatable reflector balloon, which may be on the same catheter or alternatively be on separate catheters. The reflector balloon may have an inflated diameter in a range of 2.5 to 4 mm and on its proximal surface have a shape such as a concave curvature that focuses reflected waves on to the target ablation zone. The reflector balloon is located distal to the transducer and is inserted in the narrower intercostal vein, while the ultrasound transducer remains in the larger azygos vein. The ultrasound transducer may be exposed to blood flow in the azygos vein or alternatively may be contained in a chamber in an inflatable balloon filled with coolant (e.g., circulating coolant such as sterile water or saline). The ultrasound energy is directed toward the distal reflector balloon and reflected and focused into tissue surrounding the splanchnic nerve. The advantage of this approach is that an active ultrasound transducer can be made larger and is not required to go through the sharp turn from azygos to intercostal vein. A second advantage is that several intercostal veins can be used to target ablation with the same catheter.

The catheter 220 may have a distal radiopaque marker 230 positioned distal to the ablation elements, for example distal to the balloon 221 and a proximal radiopaque marker positioned proximal to the ablation elements, for example proximal to the balloon. The distal and proximal radiopaque markers may be separated along the longitudinal axis of the shaft by a distance in a range of 5 mm to 25 mm (e.g., 10 mm to 15 mm).

FIGS. 8A to 10 illustrate exemplary ablation catheters. The ablation catheters in these examples includes an ablation element that includes first and second flexible coiled ablation electrodes that are axially spaced. It may be beneficial to have first and second electrodes rather than a single longer electrode to avoid a tendency of the single longer electrode to heat tissue mostly towards one end of the electrode. Having more than one electrode thus can help to create a long and consistent ablation in tissue. FIGS. 8A to 10 are thus examples of ablation catheters that can more consistently create a continuous ablation of the desired length, such as 10 mm to 25 mm, such as 15 mm to 25 mm, such as 15 mm to 20 mm.

An additional exemplary benefit of having first and second electrodes versus a single longer electrode is that only a single relatively shorter electrode may be energized rather than a single longer electrodes. This can be advantageous when the patient's anatomy requires or may benefit from making shorter ablations, such as if the azygos is right centered. In these cases, a longer single electrode may make it difficult or dangerous to safely ablate tissue while avoiding non-target structures. This is described in more detail elsewhere herein.

Additionally, FIGS. 8A to 10 illustrate ablation catheters that have first and second ablation elements axially separated by a gap or spacing. This gap is small enough (i.e., not too large) such that a continuous lesion is formed when energizing the first and second ablation elements, yet is large enough to avoid short circuiting.

Design features of distal sections of ablation catheters herein (e.g., FIGS. 8A to 10) thus provide exemplary benefits that allow the distal section to be advanced into position in an intercostal vein and reliably create a continuous ablation of at least 10 mm to 25 mm in length, while allowing shorter ablation sections if needed based on the patient's anatomy.

In some methods of use, the ablation energy is RF, and an energy delivery controller is adapted to deliver RF power in a range of 15 W to 50 W. In some embodiments, the controller is adapted to deliver RF power in a range of 15 W to 40 W, in a range of 15 W to 35 W, or in a range of 20 W to 35 W, such as about 25 W, about 30 W or about 35 W.

In some methods of use, energy is delivered over a period of time between 25 seconds and 120 seconds. For example, energy may be delivered for 90 seconds, for 100 seconds, for 110 second, or for 120 seconds, wherein for a portion (e.g., half) of the period of time energy, may be delivered to a first electrode and for the remainder (e.g., half) of the period energy may be delivered to a second electrode.

In some methods of use, an irrigation flow rate is from 10 mL/min to 20 mL/min, such as 10 mL/min, 15 mL/min, or 20 mL/min. With devices and methods disclosed herein, the TSN may be ablated in a relatively safe manner, with minimal or reduced adverse effects (such as damage to the lungs or other nerves). Some method of use embodiments herein may temporarily occlude blood flow and reduce an effect of vein collapse, thus advantageously avoiding challenges of a changing thermal and electrical environment during the heating process. Some method of use embodiments herein may ablate a nerve up to 5 mm from the target vessel. Some of the devices herein are dimensioned and configured for delivery and positioning in vasculature specified for ablating a target nerve (e.g., TSN, GSN).

Some of the devices herein may have one or more features that provides for a safe delivery to the target vessel.

Some of the devices and methods of use herein may safely deliver energy with temperature monitored energy delivery.

Some of the methods of use herein may generate a lesion capable of targeting a nerve up to 5 mm away from the target vessel and within a target region having a continuous lesion length from 5 mm to 25 mm, such as 10 mm to 25 mm, such as 15 mm to 20 mm, (e.g., 15 mm, 16 mm, 17 mm, 18 mm, 19 mm, 20 mm), with a single positioning and delivery of energy.

Some of the devices and methods herein are adapted to avoid risks of boiling, hot spots, or erratic energy delivery that could decrease ablation efficacy. Furthermore, some embodiments may include nerve stimulation to identify a target nerve or non-target nerve to confirm positioning prior to ablation, or to confirm technical success during or following ablation.

It may be preferred, but not required, that the methods of ablation create a continuous ablation zone (i.e., not having separate, discrete regions of ablated tissue that are not connected to each other). This ensures that the region of tissue where the target GSN nerve or GSN nerve root is likely to be located is most likely to be effectively ablated by the ablation energy. The continuous ablation zone may be circumferential, or less than circumferential.

Optionally, an ablation confirmation test can then be performed, for example, by delivering a nerve stimulation signal. Monitoring can be performed for a physiological response (e.g., splanchnic vasoconstriction, increased heart rate, increased blood pressure) to the ablation confirmation test. If the physiological response demonstrates that the first lesion did not provide a clinically significant amount of GSN blocking (e.g., by observing a lack of physiological response) then ablation energy can be delivered from the ablation catheter to create a second lesion in tissue up to 5 mm from the second intercostal vein. The distal section of the ablation catheter can be moved to a third intercostal vein that is superior to (e.g., superior and adjacent to) the second intercostal vein. The same or different ablation confirmation test can be performed, followed by another monitoring test. If the physiological response demonstrates that the first lesion and second lesion did not provide a clinically significant amount of GSN blocking (e.g., by observing a lack of physiological response) then ablation energy can be delivered from the ablation catheter to create a third lesion in tissue up to 5 mm from the third intercostal vein. Any of the ablation confirmation tests may comprise delivering a nerve stimulation signal from a stimulation electrode positioned on the distal section of the ablation catheter configured to generate an action potential in the thoracic splanchnic nerve. Alternatively or in addition to, the ablation confirmation test may comprise a leg raise test. Alternatively or in addition to, the ablation confirmation test may comprise adding fluid volume to the venous system. Alternatively or in addition to, the ablation confirmation test may comprise a hand-grip test. Alternatively or in addition to, the ablation confirmation test may comprise measuring venous compliance or capacitance.

In exemplary methods in which an ablation confirmation test includes a leg raise test, the method may comprise any of the following steps. Prior to ablation in the lowest intercostal vein, a baseline measurement may be obtained by raising the legs and measuring the change in central venous pressure and waiting for equilibration, that is a measure of the total venous compliance including the central veins and splanchnic bed. The legs can then be lowered, to allow equilibration so blood redistributes back to the legs. An ablation in the lowest intercostal vein (e.g. T11) can then be performed as set forth herein. The legs can then be raised, followed by waiting for equilibration and re-measure central venous pressure. A measurement can then be made to determine if there was an appropriate reduction in total venous compliance. If yes, then the GSN has successfully been ablated. If no, then an ablation in the next higher intercostal vein (e.g., T10) can be performed, as set forth herein. The measurement can be repeated. A determination can then be made to see if there was an appropriate reduction in total venous compliance. If yes, then the GSN has successfully been ablated. If no, then an ablation in the next higher intercostal vein (e.g., T9) can be performed.

In exemplary methods in which an ablation confirmation test comprises a hand-grip or other activity that increases sympathetic nervous system (SNS) outflow to the splanchnic bed may comprise the following steps. An ablation can be performed in a lowest intercostal vein (e.g., T11). Venous compliance can then be measured. A hand-grip can then be performed for a predetermined amount of time (e.g., 60 seconds). Venous compliance can then be remeasured. If there is no change in venous compliance, the initial ablation was sufficient to achieve a clinically significant outcome. If there still is a decrease in compliance, some of the SNS activity caused by the hand-grip is getting through. The ablation in the lowest intercostal vein was thus insufficient to achieve a clinically significant effect. An ablation in the next higher intercostal vein (e.g., T10) can then be performed. A hand grip test for a predetermined amount of time (e.g., 60 seconds) can be performed. Venous compliance can then be remeasured. If there is no change in compliance, the second ablation was sufficient. If there is a decrease in compliance, some of the SNS activity caused by the hand-grip is getting through, and the ablation in the next higher intercostal vein was thus insufficient to achieve a clinically significant effect. Ablation is the next higher intercostal vein (T9) can then be performed. The procedure is done at this point as ablation at a level higher than the 3rd lowest intercostal vein is not anticipated.

In any of the methods herein, including ablation confirmation tests herein, not all of the steps need necessarily to be performed. And some of the steps may occur in different orders. It is of note that the procedures herein are intending to target particular nerves or nerve roots, and are doing so from particular target veins, and even within those veins are placing ablation elements or members within certain regions. The anatomical regions that are being accessed and targeted necessitate certain design requirements. In other treatments that are targeting different anatomical locations for placement, and targeting different target nerves, the device design constraints for those approaches are very different, and thus the devices that can be used in those treatments may be very different. The disclosure herein thus provides specific reasons for designing particular devices, and those reasons include being able to effectively carry out the treatments specifically set forth herein.

While the above description provides examples of one or more processes or apparatuses, it will be appreciated that other processes or apparatuses may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

Specific embodiments described herein are not intended to limit any claim and any claim may cover processes or apparatuses that differ from those described below, unless specifically indicated otherwise. The claims are not limited to apparatuses or processes having all of the features of any one apparatus or process described below or to features common to multiple or all of the apparatuses described below, unless specifically indicated otherwise. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

ADDITIONAL EXAMPLES

A first additional example is a method of characterizing the position of a patient's azygos vein relative to a portion of the patient's spine, comprising: while imaging at least a portion of the patient's spine: intravascularly delivering a device into a patient's azygos vein: performing at least one of: injecting a radiopaque contrast agent (e.g., dye) from the device into the patient's vasculature (e.g., into the azygos vein and/or one or more intercostal veins) to visualize the vasculature relative to a position of the spine, or identifying the position of at least a portion of the device relative to a portion of the spine, to thereby characterize (e.g., qualify and/or quantify) the position of the patient's azygos vein relative to a portion of the spine (e.g. relative to a midline of the spine).

In this first additional example, imaging may comprise imaging in an anterior-to-posterior view.

This first additional example may further comprise determining a lateral position of a patient's azygos vein, where it meets an intercostal vein, relative to the patient's spine. Determining a lateral position of the patient's azygos vein may be performed while imaging the patient's azygos vein. Imaging may comprise radiographic imaging (e.g. fluoroscopy) after injecting a radiopaque contrast agent (e.g., dye) from the device into the patient's vasculature. Determining a lateral position may be used to determine where to place an ablation catheter relative to the intercostal vein, as part of an ablation procedure (optionally to ablate a GSN).

A second additional example is a method that includes assessing a position of a patient's azygos vein to determine if it is centered, right-biased (to the patient's right of center), or left-biased (to the patient's left of center). Assessing a position of the patient's azygos vein may be performed while imaging the patient's azygos vein. Imaging may comprise radiographic imaging (e.g. fluoroscopy). Imaging may comprise imaging in an anterior-to-posterior view. Assessing the position may be used to determine where to place an ablation catheter as part of an ablation procedure (optionally intended to ablate a GSN).

In this second additional example, an assessing step can be used to determine where to place a radiopaque marker of an ablation catheter (optionally a proximal radiopaque marker), wherein the ablation catheter includes an ablation element distal to the radiopaque marker.

In this second additional example, the assessing step is used to determine whether to place the radiopaque marker at an ostium where the azygos vein meets an intercostal vein, or at (including substantially at) a midline of the spine.

In this second additional example, if an assessing step indicates that the azygos vein is right-biased or centered (including substantially centered), the method may include positioning the radiopaque marker at an ostium where the azygos vein meets the intercostal vein.

In this second additional example, if the assessing step indicates that the azygos vein is left-biased, the method may include positioning the radiopaque marker at or substantially at a midline of the spine (for example, as determined in an anterior-to-posterior imaging view).

In this second additional example, the assessing step may be used to determine where to place an ablation element (e.g. one or more electrodes) that is part of the ablation catheter.

In this second additional example, the method may further comprise assessing a position of a distal radiopaque marker relative to at least one or more of a portion of the spine, a rib, or a costovertebral joint. The method may further comprise retracting the ablation catheter proximally if the assessment indicates that the distal radiopaque marker is positioned too far distally, which thereby indicates the ablation element is positioned too far distally. The method may further ensure that the distal radiopaque marker is not further distally than the costovertebral joint.

A third additional example is a method of intravascularly positioning an ablation catheter for GSN ablation, comprising: positioning an ablation catheter in one or more of an intercostal vein (e.g. T9, T10, or T11) and an azygos vein, wherein the position of the ablation catheter is selected based on a characterized relative position of a portion of the spine and a location of the azygos vein where it meets the intercostal vein.

A fourth additional example is a method of characterizing a position of a distal section of an ablation catheter to facilitate placement of at least a portion of the ablation catheter in an intercostal vein, comprising: positioning an ablation catheter in a patient's intercostal vein (e.g. a T9, T10, or T11 intercostal vein); while imaging a portion of the patient that includes the intercostal vein and a portion of the spine, determining a location of one or more components of the ablation catheter relative to one or more of a portion of the spine, a rib, or a costovertebral joint.

A fifth additional example is a method of any claim herein, comprising accessing venous vasculature at the patient's jugular vein or femoral vein with an access introducer sheath (e.g. 12F).

A sixth additional example is a method of any claim herein, comprising delivering a delivery sheath (e.g., 9F sheath) to an azygos vein (e.g., to one or two thoracic levels above the target intercostal).

A seventh additional example is a method of any claim herein, comprising delivering contrast agent to show a location of an azygos vein and one or more intercostal veins while imaging the azygos vein and one or more intercostal vein.

Any of additional examples may include an imaging step that comprises imaging in an anterior-to-posterior direction (e.g. with a C-arm in an AP position).

Any of additional examples may include positioning a C-arm in a Right Anterior Oblique angle.

Any of additional examples may include positioning a C-arm in a range of 20 degrees to 70 degrees, such as 30 to 60 degrees.

Any of additional examples may include positioning a C-arm at an angle that maximizes a projected distance between first and second axially spaced locations on the ablation catheter (e.g. locations of proximal and distal radiopaque markers).

Any of additional examples may include assessing if a RO marker (e.g., a distal RO marker) is at or proximal to a particular anatomical location (e.g. a costovertebral joint).

Any of additional examples may include, if the marker is at or proximal to the particular anatomical location, continuing with an ablation procedure (e.g. ablating tissue). If the marker is not at or proximal to the particular anatomical location, the method may include moving the ablation catheter within the intercostal vein. If the marker is not at or proximal to the particular anatomical location, the method may include generating ablative energy within a proximal ablation element (e.g. coiled electrode) but not with a distal ablation element (e.g. coiled electrode).

An eighth additional example is an ablation catheter sized and configured such that a distal section of the ablation catheter can be advanced into a T9, T10, or T11 intercostal vein from an azygos vein, and adapted to deliver ablative energy, comprising: an elongate shaft with a length such that a distal section of the catheter can be positioned in a T9, T10, or T11 intercostal vein; and the distal section comprising an electrically conductive flexible ablation element carried by the elongate shaft, the electrically conductive flexible ablation element (which may comprise more than one ablation element) having a length from 5 mm-20 mm, and the distal section having an OD (at least in a delivery configuration) from 1.5 mm-3 mm.

A ninth additional example is an ablation catheter sized and configured such that a distal section of the ablation catheter can be advanced into a T9, T10, or T11 intercostal vein from an azygos vein, and adapted to deliver ablative energy, comprising: an elongate shaft with a length such that a distal section of the catheter can be positioned in a T9, T10, or T11 intercostal vein; and the distal section comprising an electrically conductive flexible ablation element carried by the elongate shaft.

In this ninth additional example, the ablation element may comprise a first ablation element axially spaced from a second ablation element, the first and second ablation elements carried by the shaft. The first ablation element may have a coiled configuration, and wherein the second ablation element may have a coiled configuration. A coiled configuration of the first ablation element may be the same in all regards as a coiled configuration of the second ablation element. A coiled configuration of the first ablation element may be different than a coiled configuration of the second ablation element in at least one way.

In this ninth additional example, the first ablation element may have a different length than the second ablation element.

In this ninth additional example, the first ablation element may have a different coil direction (e.g. left handed vs right handed) than the second ablation element.

In this ninth additional example, the first ablation element may have a different pitch than the second ablation element.

In this ninth additional example, the first ablation element may have a different wire thickness than the second ablation element.

In this ninth additional example, an OD of the distal section at the location of the first ablation element may be different than an OD of the distal section at the location of the second ablation element.

In this ninth additional example, a first ablation element and a second ablation element may each have either a curvilinear (e.g. circular) or rectilinear (e.g., rectangular) cross sectional outer profile.

In this ninth additional example, a first ablation element and a second ablation element may be a superelastic material such as nitinol.

In this ninth additional example, a first ablation element and a second ablation element may be sufficiently flexible to allow the distal section to be advanced from an azygos vein into one of a T9, T10, or T11 intercostal vein.

In this ninth additional example, at least one of a first and second ablation elements may be made from a laser cut tubular element (e.g., a nitinol tube).

In this ninth additional example, at least one of a first and second ablation elements may comprise a wire mesh or braid.

In this ninth additional example, at least one of a first and second ablation elements may be a ring electrode having a length not more than 5 mm, optionally around 3 mm.

In this ninth additional example, each of a first and second ablation elements may have a length from 1 mm-12 mm, optionally from 2 mm-12 m, optionally from 5 mm-12 mm, optionally from 6 mm-11 mm, optionally from 7 mm-10 mm, such as around 8 mm.

In this ninth additional example, an axial spacing between a first and second ablation elements may be from 0 mm-8 mm, such as from 0 mm-5 mm, such as from 0.5 mm-5 mm, such as from 1 mm-4 mm.

In this ninth additional example, an ablation element total axial length may be from 1 mm-25 mm, optionally from 2 mm-22 mm, optionally from 5 mm-20 mm, optionally 8 mm-20 mm, optionally 10 mm-20 mm, optionally 10 mm-18 mm, optionally, preferably 10 mm-15 mm.

In this ninth additional example, the ablation element, and optionally both of a first and second ablation elements, may have an expandable diameter.

In this ninth additional example, the ablation element may comprise a plurality of ablation elements, of which first and second ablation elements may be part of and may define the entirety of the plurality of ablation elements.

In this ninth additional example a plurality of ablation elements may be configured to be independently energized in monopolar mode (with a ground pad).

In this ninth additional example, any two of a plurality of ablation elements may be configured to be energized in bipolar mode.

In this ninth additional example, the catheter may include a temperature sensor disposed between the first and second ablation elements and carried by the shaft.

In this ninth additional example, the catheter may further comprise one or more of a temperature sensor distal to a distal ablation element, or a temperature sensor proximal to a proximal ablation element.

In this ninth additional example, the catheter may include at least one irrigation port in fluid communication with an irrigation lumen that is connectable to a fluid source at a proximal region of the ablation catheter. The ablation catheter may further comprise a second irrigation port distal to the proximal ablation element.

In this ninth additional example, the catheter may include one or more irrigation ports between a distal end and a proximal end of a distal ablation member, optionally between the windings of a coiled distal ablation member.

In this ninth additional example, the catheter may comprise one or more irrigation ports between a distal end and a proximal end of a proximal ablation member, optionally between the windings of a coiled proximal ablation member.

In this ninth additional example, the catheter may include one or more irrigation ports under any of the flexible ablation elements, such as a distal ablation element and/or a proximal ablation member.

In this ninth additional example, the catheter may further comprise a deployable element carried by the shaft (optionally expandable). A deployable element may be distal to the ablation element, optionally distal to a distal ablation element. A deployable element may be inflatable, and wherein the shaft may include an inflation port within the inflatable deployable element. A deployable element may have a delivery configuration and a deployed configuration with an OD greater than the delivery configuration. A deployable element may have an OD from 3-6 mm in the deployed configuration, such as 4 mm-6 mm. A deployable element may have an OD that is equal to or greater than the OD of the shaft in the distal section by no more than 0.2 mm. A deployable element may comprise at least one of the following: a balloon, a bellowed member, or a coated stent or coated stent-like device (e.g., a reinforcing member coated with a one or more layers of material).

In this ninth example, the ablation catheter may further comprise a proximal deployable element carried by the shaft proximal to the ablation element, which may be proximal to a proximal ablation element. A proximal deployable element may be inflatable, and wherein the shaft may include an inflation port within the proximal deployable element. A proximal deployable element may have a delivery configuration and a deployed configuration with an OD greater than the delivery configuration. A deployable element may have an OD from 4-10 mm in the deployed configuration, and optionally larger than an OD of a distal deployable member. A proximal deployable element may have an OD that is equal to or greater than the OD of the shaft in the distal section by no more than 0.2 mm. A proximal deployable element may comprise at least one of the following: a balloon, a bellowed member, or a coated stent or coated stent-like device (e.g., a reinforcing member coated with a one or more layers of material).

In this ninth additional example, the catheter may include a central deployable element. A central deployable element may include any of the features, including any combination thereof, of a distal or proximal deployable member herein.

In this ninth additional example, the catheter is configured for transvascular ablation of a GSN. The ablation catheter may include a distal section that includes the distal-most 7 cm of the ablation catheter. The ablation element may be adapted to create an ablation having a length in a range of 5 mm to 25 mm.

In this ninth additional example, a distal section may be adapted for flexibly traversing a bend from an azygos vein to a T9-T11 intercostal vein (e.g., having a radius of curvature>=5 mm, angle as much as 120 degrees.

In this ninth additional example, an outer diameter of the distal section (at least in a delivery state) is in a range of 1.5 to 3 mm.

In this ninth additional example, the ablation catheter may further comprise a guidewire lumen within the elongate shaft.

In this ninth additional example, a total length of the ablation element (which may comprise a plurality of individual ablation elements) may be from 5 mm to 20 mm, such as 10 to 15 mm.

In this ninth additional example, any of the ablation elements may comprise one or more of an RF ablation electrode, a coiled wire electrode, a laser cut RF electrode, a RF electrode printed with conductive ink, a RF electrode on an expandable balloon (e.g., conductive ink, flexible circuits), a conductive membrane RF electrode, a RF electrodes on an expandable cage or mesh, an ultrasound ablation transducer, an electroporation electrodes, an cryoablation element, or a virtual RF electrode.

In this ninth additional example, the ablation element may be adapted to deliver ablation energy circumferentially (radially symmetric around the ablation element/around the vessel).

In this ninth additional example, the catheter may further include a proximal radiopaque marker positioned on the shaft at or proximal to a proximal end of the ablation element.

In this ninth additional example, the catheter may further a distal radiopaque marker positioned on the shaft distal to a distal end of the ablation element(s).

In this ninth additional example, the catheter may include an axial space between a distal radiopaque marker and a distal end of the ablation element.

Any of the methods in any of the additional methods may be used with any of catheters in the additional examples. Any of the catheters in the additional examples may be used with methods herein or used in ways that are not described herein.

What is claimed is:

1. A method of characterizing a position of a human patient's azygos vein relative to a portion of the patient's spine, comprising:
    imaging at least one radiopaque device, positioned in the azygos vein and/or in an intercostal vein, relative to a portion of the spine, using a radiographic imaging device, to thereby characterize the position of the patient's azygos vein relative to a midline of the spine; and
    determining if the azygos vein is centered, left-biased or right biased with respect to midline of a vertebra based on one or more images generated by said imaging device; and
    subsequent to determining whether the azygos vein is centered, left-biased or right biased with respect to the midline of the vertebra, in the patient whose azygos vein is determined to be left-biased with respect to the midline of the vertebra and not centered or right biased with respect to the midline of the vertebra, positioning a distal end of an energy delivery device in the intercostal vein and positioning a radiopaque marker at the midline of the vertebra.

2. The method of claim 1, wherein positioning the radiopaque marker at the midline of the vertebra comprises distally advancing the radiopaque marker to the midline of the vertebra.

3. The method of claim 1, wherein positioning the radiopaque marker at the midline of the vertebra comprises positioning the radiopaque marker within the intercostal vein distal to an ostium of the intercostal vein.

4. The method of claim 1, wherein the energy delivery device further comprises an ablation element distal to the radiopaque marker, wherein positioning the radiopaque marker at the midline of the vertebra comprises positioning the ablation element in the intercostal vein.

5. The method of claim 4, wherein positioning the radiopaque marker comprises positioning the ablation element in a T9, T10, or T11 intercostal vein.

6. The method of claim 4, wherein positioning the radiopaque marker positions the ablation element proximal to a sympathetic trunk.

7. The method of claim 4, wherein positioning the radiopaque marker positions the ablation element between an ostium of the intercostal vein and a sympathetic trunk.

8. The method of claim 4, further comprising delivering ablation energy using the ablation element to ablate a greater splanchnic nerve.

* * * * *